United States Patent [19]
Charnock-Jones et al.

[11] Patent Number: 6,121,230
[45] Date of Patent: Sep. 19, 2000

[54] ANTI-VEGF AGENTS IN THE TREATMENT OF ENDOMETRIOSIS

[75] Inventors: David Stephen Charnock-Jones; John McLaren, both of Cambridge; Andrew Prentice, Milton; Stephen Kevin Smith, Cambridge, all of United Kingdom

[73] Assignee: Metris Therapeutics Limited, London, United Kingdom

[21] Appl. No.: 08/750,143

[22] PCT Filed: May 26, 1995

[86] PCT No.: PCT/GB95/01212

§ 371 Date: May 9, 1997

§ 102(e) Date: May 9, 1997

[87] PCT Pub. No.: WO96/32708

PCT Pub. Date: Dec. 7, 1995

[30] Foreign Application Priority Data

May 26, 1994 [GB] United Kingdom .................... 9410533

[51] Int. Cl.[7] .......................... A61K 38/17; A61K 39/395
[52] U.S. Cl. .......................... 514/2; 424/134.1; 424/158.1; 530/300; 530/350; 530/387.1
[58] Field of Search ................................ 514/44, 2; 435/6, 435/91.31, 325, 366; 536/24.5; 530/350, 300

[56] References Cited

PUBLICATIONS

Society for the study of Reproduction, Biology of Reproduction vol. 58, Suppl. 1, p213, Abstract #:454, 1998.

Osteen et al., Seminars in Reproductive Endoinology 14(3):247–255, Aug. 1996.

Burner et al. Metalloproteinases and Experimental Edometriosis vol. 99 (12), pp. 2851–2857, Jun. 1997.

Stall et al. Pharm. Res. 12:465–483 (1995).

Gewirtz et al PNAS 93:3161–3163 (1996).

Rojanasakul Advanced Drug Del. Reviews 18:115–131 (1996).

*Primary Examiner*—John L. LeGuyader
*Attorney, Agent, or Firm*—Klauber & Jackson

[57] ABSTRACT

Disclosed are: a composition for use in the treatment of endometriosis, comprising an agent capable of interfering with the production and/or activity of VEGF, and a physiologically acceptable carrier substance; a composition for the treatment of endometriosis comprising an agent which inhibits the activation and/or recruitment of peritoneal macrophages, and a physiologically acceptable carrier; and method of making the compositions and their use in the treatment of endometriosis.

4 Claims, 23 Drawing Sheets

Graph showing % KDR positive peritoneal macrophages in women with and without endometriosis throughout the cycle + $P < 0.01$. Significantly different from normal proliferative ++ $P < 0.01$. Significantly different from endometriotic proliferative

* $P < 0.01$. Significantly different from normal secretory

Distribution of VEGF concentration in PF of individuals with and without endometriosis

FIG. 12

3H Thymidine incorporation in HUVEC Following Exposure to Peritoneal Macriphages Conditioned Media

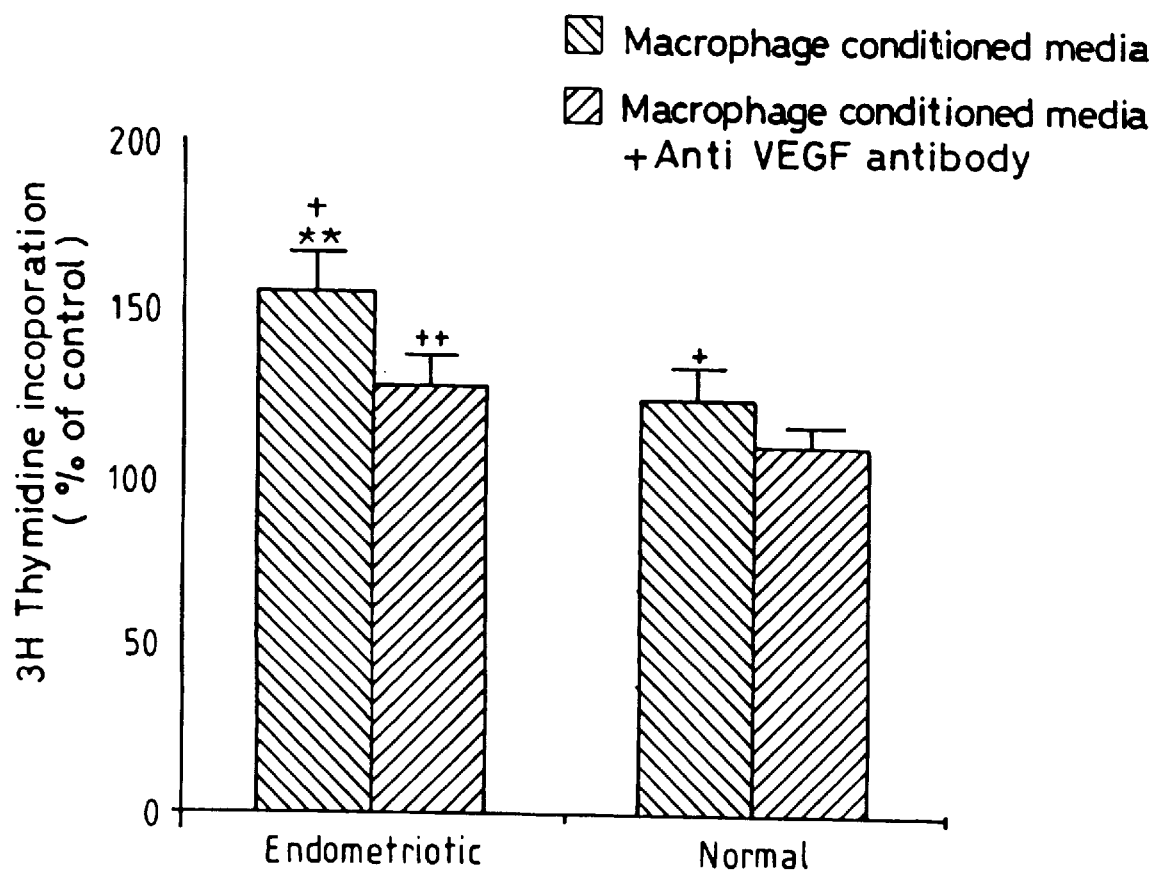

Peritoneal macrophage conditioned media

+ = significantly greater compared ($P < 0.05$) to control conditioned media

** = significantly greater compared ($P < 0.05$) to normal macrophage conditioned media ++ = significantly less ($P < 0.05$) than endometriotic macrophage conditioned media

ANTI-VEGF AGENTS IN THE TREATMENT OF ENDOMETRIOSIS

This application is a 371 of International Application PCT/GB95/01212, filed May 26, 1995.

FIELD OF THE INVENTION

This invention relates to the discovery of expression of vascular endothelial growth factor (VEGF) and its associated receptors (Flt and KDR) in certain tissues and as a consequence demonstrates the potential for VEGF antagonists in the treatment/prevention of endometriosis and related conditions.

BACKGROUND OF THE INVENTION

Endometriosis is defined as the presence of endometrial cells outside of the uterine cavity. The disease affects women during their childbearing years with deleterious social, sexual and reproductive consequences. The development and maintenance of endometriosis involves the establishment and subsequent sustained growth of endometrial cells at ectopic sites, most commonly the pelvic peritoneum, following retrograde menstruation (Sampson 1927 Am. J. Obstet. Gynecol. 14, 422; Ridley & Edward 1958 Am. J. Obstet. Gynecol. 76, 783–790; Lieu & Hitchcock 1968 Br. J. Obstet. Gynecol. 93, 859–862; and Thomas & Prentice 1992 Repro. Med. Rev. 1, 21–36). Except for the influences of ovarian steroid hormones (Dizerega et al., 1980 Fertil. Steril. 33, 649–653; Bergqvist et al., 1985 Am. J. Pathol. 121, 337–341) little is known about the factors that control this disease. However, it may be that the growth of ectopic endometrial implants is influenced by angiogenic growth factors (angiogenesis being the name given to the formation of new blood vessels).

Endometriotic lesions are characterised by hypervascularisation both within the endometriotic tissue and in the surrounding peritoneum (Shaw, p46–47 "An atlas of endometriosis" 1993, The Parthenon publishing group; and Folkman & Shing 1992 J. Biol. Chem. 267, 10931–10934). Vascular endothelial growth factor (VEGF) is a recently characterised angiogenic protein being a potent mitogen for endothelial cells and a mediator of vessel permeability (Ferrara et al., 1992 Endocrinol. Rev. 13, 18–32). VEGF and its receptors flt and KDR, which are expressed on endothelial cells, (De Vries et al., 1992 Science 255, 989–991) have been implicated in angiogenesis in the developing embryo (Breier et al., 1992 Development 114, 521–532; Jakeman et al., 1993 Endocrinology 133, 848–859; and Millauer et al., 1993 Cell 72, 835–846) and in adult tissue undergoing profound angiogenesis such as eutopic endometrium (Chamock-Jones et al., 1993 Biol. Repro. 48, 1120–1128) and the lutenised corpus luteum (Ravindranath et al., 1992 Endocrinology 13, 254–260). In addition, its role in tumour angiogenesis is becoming well established (Shweiki et al., 1992 Nature 359, 843–848; Kim et al., 1993 Nature 362, 841–844).

The present inventors sought to determine whether VEGF and its associated receptor flt are present in endometrial tissue. In addition, they sought to determine whether other cells such as the peritoneal macrophages, whose numbers and activation status are known to be elevated in this disease (Halme et al., 1983 Am. J. Obstet. Gynecol. 145, 333–337; Olive et al., 1985 Fertil. Steril. 44, 772–777; and Halme et al., 1987 Am. J. Obstet. Gynecol. 156, 783–789), may also be involved in the pathogenesis of endometriosis through the secretion of VEGF.

SUMMARY OF THE INVENTION

In a first aspect the invention provides a composition for use in the treatment of endometriosis, comprising an agent capable of interfering with the production and/or activity of VEGF, and a physiologically acceptable carrier substance.

It will be apparent that there are many possible agents for use in compositions in accordance with the invention, which could vary considerably in their nature, depending on the mode of action of the selected agent.

For example, agents could be used to block VEGF production systematically or, preferably, locally (i.e. in or around the endometriotic tissue). Desirably, one might use an agent to block VEGF production by local macrophages, which seems to play a particularly important role in pathogenesis. It has been shown that VEGF expression may be regulated by steroids (e.g. Charnock-Jones et al., 1993 Biology of Reproduction 48, 1120–1128), and it is suspected that macrophages possess steroid receptors. Thus substances which regulate steroid pathways might be useful in down-regulating VEGF production, especially in macrophages. A number of steroids and steroid inhibitors are known (e.g. oestrogens and the anti-oestrogen Tamoxifen; progesterone and the anti-progestogen RU 486).

Alternative agents include VEGF anti-sense RNA or ribozymes (e.g. Zaug et al., 1986 Nature 324, 429–433), either of which could be used specifically to inhibit the translation of VEGF mRNA, which specific approach is desirable compared to less targeted agents.

Other agents could be used to block or inhibit the activity of VEGF. These include, for example: anti-VEGF antibodies (or effective portions thereof, such as Fv, Fab or scFv portions) to inhibit VEGF binding to KDR and/or flt receptors (e.g. as described in WO 94/10202); VEGF antagonists, which could compete with VEGF for binding to KDR and/or flt receptors (e.g. soluble truncated forms of flt receptor, which bind to VEGF, as described, for example, in WO 94/21679); and tyrosine kinase inhibitors, which could be introduced into the cells upon which VEGF exerts its effects—preferably these take the form of comparatively small peptides (conveniently, synthetic peptides), or agents which can be packaged in particles (such as liposomes) which advantageously will be phagocytosed by macrophages.

Yet other groups of agents could be used to inhibit flt and/or KDR expression in the cells in and around the endometriotic tissue. Such agents could include anti-sense RNA or ribozymes specifically to inhibit the translation of flt and/or KDR mRNA, or agents to be used in gene therapy methods. As an example of the latter category, one could introduce into the appropriate target cells a "dominant negative receptor" gene (see Millauer et al., Nature 367, 576–579), typically by means of a retroviral vector, in order to prevent the cells from expressing a functional VEGF receptor.

Preferably the composition will comprise an agent which is targeted to macrophages in or around the endometriotic tissue. Advantageously, the agent will be associated with a ligand for a macrophage-specific cell surface marker (such as CD14), which can help target the agent to macrophages.

It will be appreciated that these categories of agents are not necessarily mutually exclusive, and indeed, some synergy may well result if a composition were to include two or more agents, preferably having different modes of action.

Compositions in accordance with the invention might be given systemically (e.g. i–v), or given locally. Intra-peritoneal or intra-uterine administration may well be advantageous. Appropriate doses and routes of administration could be elucidated by trial and error without requiring the exercise of inventive effort.

In a further aspect the invention provides a composition for the treatment of endometriosis comprising an agent which inhibits the activation and/or recruitment of peritoneal macrophages, and a physiologically acceptable carrier substance.

Agents having such properties include: immunomodulatory agents, such as cvytokines, which can specifically inhibit macrophage activation and/or recruitment; antibodies (or effective portions thereof) to block appropriate macrophage receptors; substances which inhibit macrophage activation/recruitment signals (e.g. antibodies, specific antagonists); or anti-sense RNA or ribozymes to prevent translation in macrophages of mRNAs which encode polypeptides leading to activation of the macrophages.

The invention thus also provides a method of treating endometriosis, comprising administering to a patient an effective amount of one or both of the compositions defined above.

In a further aspect, the invention provides a method of making a composition for use in the treatment of endometriosis, comprising mixing a physiologically acceptable carrier substance together with an agent capable of inhibiting the production and/or activity of VEGF.

In another aspect the invention provides a method of making a composition for use in the treatment of endometriosis comprising mixing a physiologically acceptable carrier substance together with an agent capable of inhibiting the activation and/or recruitment of peritoneal macrophages.

The invention will now be further described by way of illustration and with reference to the accompanying drawings, in which.

Figure 7A:
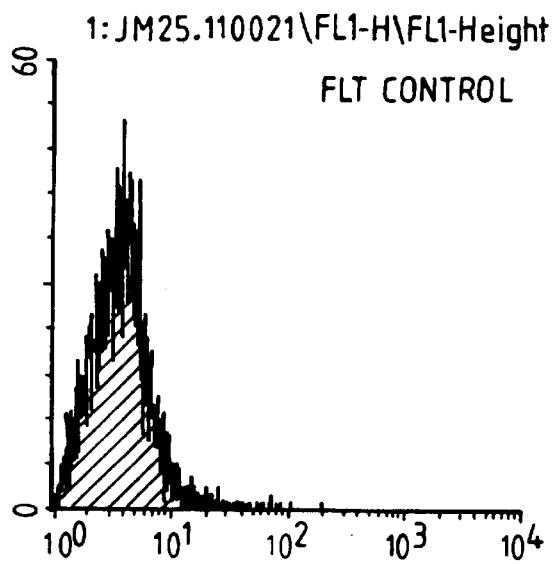
Figure 7B:
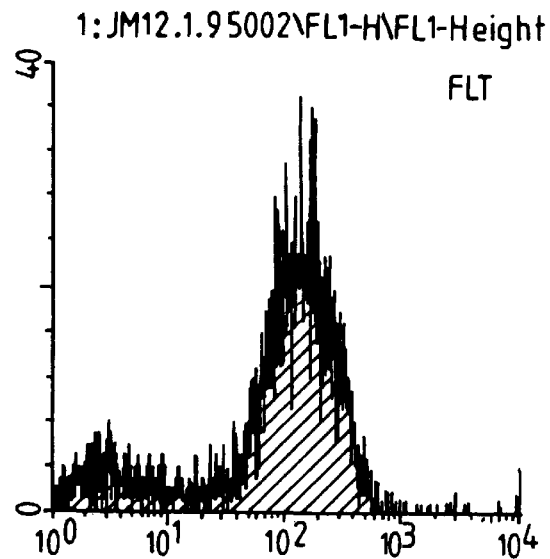
Figure 7C:
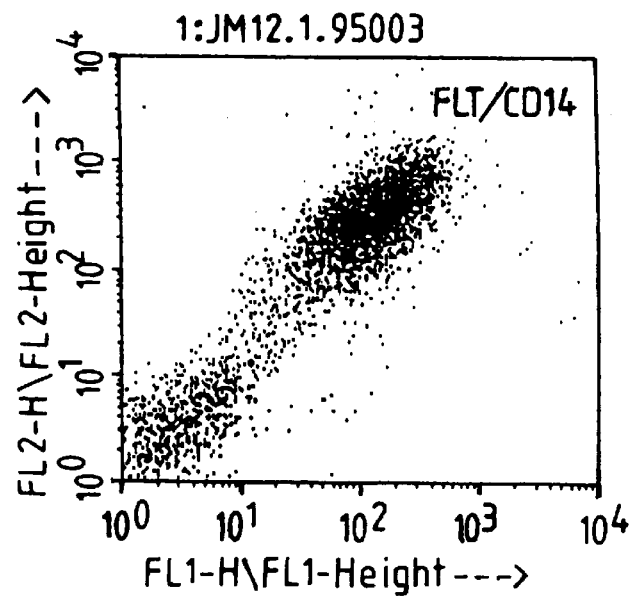
Figure 9:
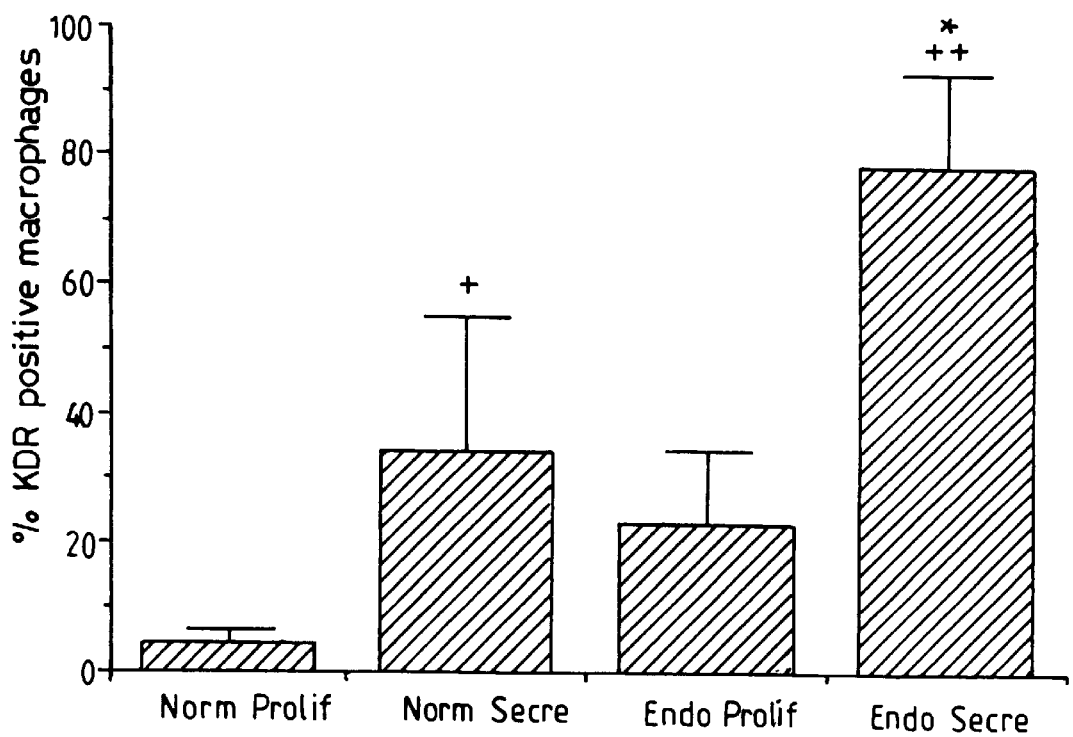
Figure 10:
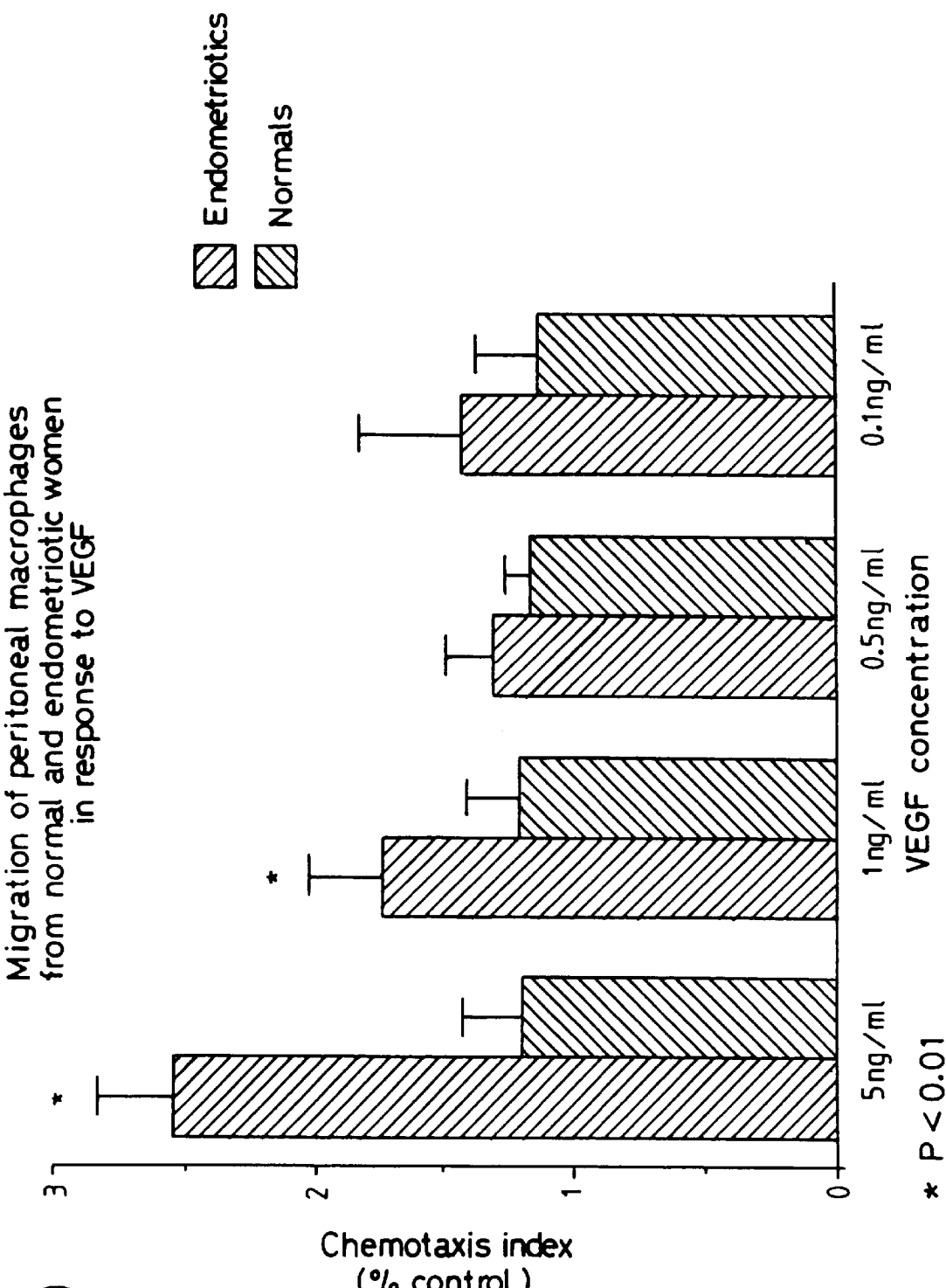
Figure 11:
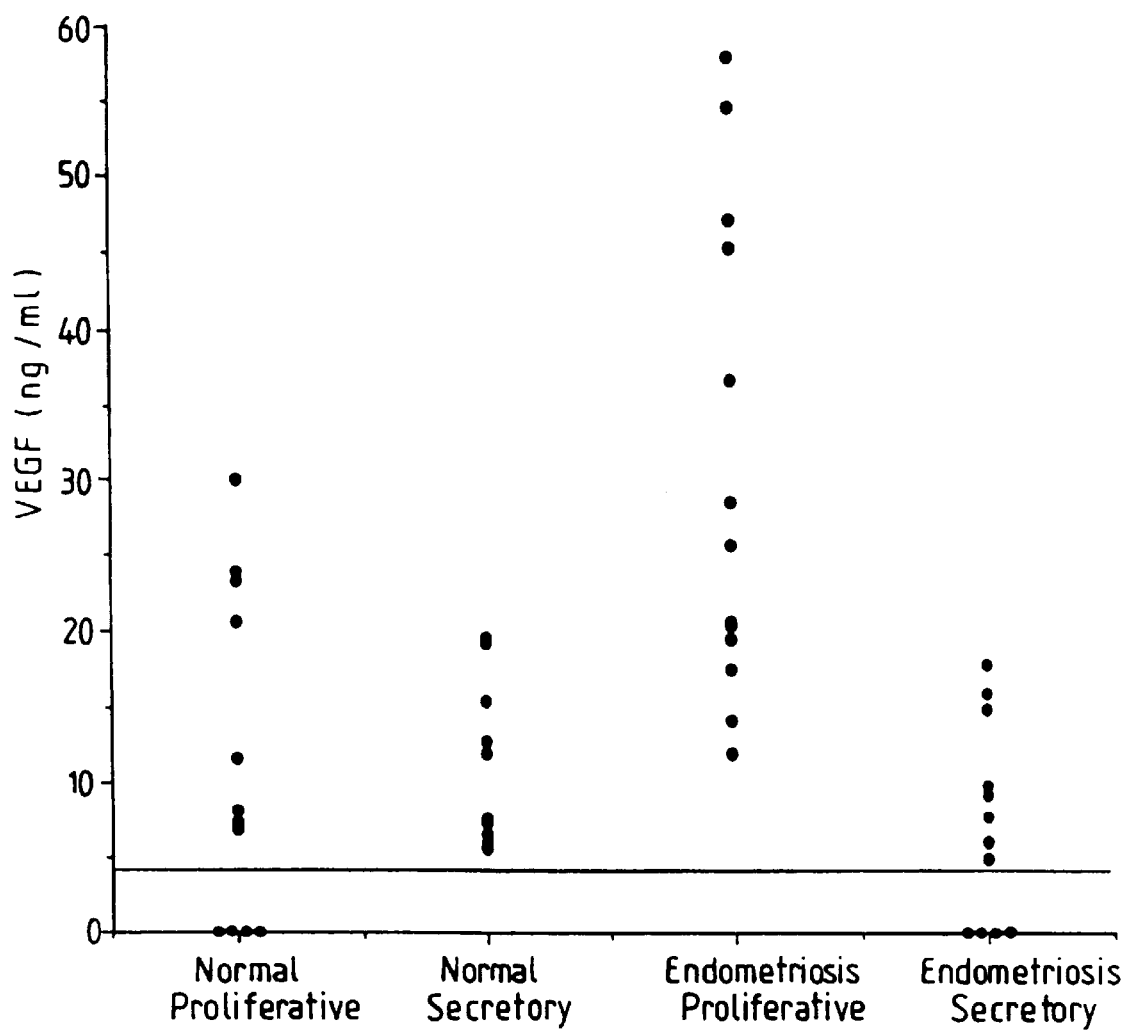

FIGS. 7 (part A–C) and 8 show graphs presenting the results of FACS analysis of peritoneal macrophages isolated from subjects, using antibody to flt or KDR;

FIG. 9 is a bar chart showing the percentage of KDR+ peritoneal macrophages isolated from endometriotic and normal subjects;

FIG. 10 is a bar chart showing the chemotactic response (migration) of peritoneal macrophages, isolated from endometriotic and normal subjects, to VEGF;

FIG. 11 is a chart showing the concentration of VEGF (ng/ml) in the peritoneal fluid of endometriotic and normal subjects; and FIG. 12 is a bar chart of $^3$H thymidine incorporation in human umbilical vein endothelial cells (HUVECs) following exposure to medium conditioned by peritoneal macrophages isolated from endometriotic or normal subjects.

EXAMPLES

Methods

Patient Details

Women between 24–44 years who were undergoing elective laparoscopy for infertility were used for this study. Patients were diagnosed as normal or endometriotic following laparoscopic investigation, and scored according to the conditions set by the American Fertility Society (AFS). Suspected endometriotic tissue was biopsied and the diagnosis confirmed histologically. Ectopic and eutopic endometrial biopsies, peritoneal fluid and peripheral blood samples were taken from each of the six endometriotic patients. Peritoneal fluid, endometrium and blood was also obtained from six cycle matched non-endometriotic controls. Table 1 shows the details of the six endometriotic patients and the results of in situ hybridisation, using probes specific for VEGF mRNA (performed as described below), in matched ectopic and eutopic endometrial tissue.

TABLE 1

| Patient | Age | Day of Cycle | AFS Score | Ectopic Tissue | Eutopic Tissue |
| --- | --- | --- | --- | --- | --- |
| 1 | 30 | 7 | II (minimal) | S/G | S |
| 2 | 24 | 10 | IV (minimal) | –ve | S |
| 3 | 30 | 14 | II (minimal) | S/G | S |
| 4 | 31 | 17 | XII (mild) | S/G | S/G |
| 5 | 44 | 22 | VII (mild) | –ve | S/G |
| 6 | 31 | 28 | I (minimal) | S/G | S/G |

S = Hybridisation in the stroma
G = Hybridisation in the glands
–ve = no hybridisation detected Isolation of Peritoneal Macrophages (PM)

Peritoneal fluid (PF) was aspirated from the posterior cul-de-sac immediately after insertion of the trocar. Samples were clarified by centrifugation at 400 g for 10 min; the supernatants were stored at –70° C. until used. Macrophages were isolated from the pellet following further centrifugation through Ficoll-Hypaque 1077 (Sigma., Poole, UK) at room temperature for 10 min at 400 g. Cells were washed in phosphate buffered saline (PBS) and counted before being resuspended at a concentration of 1×10$^6$ cells/ml in DMEM-H (Gibco., Paisley, UK) containing 5 mM Hepes, penicillin (100 mU/ml), streptomycin (100 μg/ml) and L-glutamine (2 mM). Cell suspensions were further purified by adherence to treated slides for 2 h at 37° C. in 5% $CO_2$, which allows the "sticky" macrophages to be retained on the slide whilst other leukocytes are washed away.

The purity of the preparation was determined by using non-specific esterase staining using a kit (Sigma., Poole, UK), and immunohistochemical staining with the macrophage monoclonal antibody to CD14 (Leu M3)(Dako., Cambridge, UK).

In Situ Hybridisation

In situ hybridisation was carried out according to the method of Kanzaki as described previously (Sharkey et al., 1993 Mol. Endo. 6, 1235–1241). Cryostat sections were collected onto 3-aminopropyl-triethoxysilane coated slides, air dried, and fixed in 4% paraformaldehyde in PBS for 20 min at 4° C. Slides were dehydrated through alcohols and stored at −70° C. A plasmid containing 579 bp of the coding region of VEGF was linearised with the restriction enzymes Not I or Bam I and used as templates for the generation of sense and anti-sense RNA probes, respectively. Approximately $2\times10^6$ cpm of $^{35}$S-UTP were incorporated per microgram of probe. Following acetylation, the air dried slides were prehybridised in 50% formamide, single-strength Denhardt's, (20 mM Tris-HCl (pH 8.0), 0.3M NaCl, 5 mM EDTA, 10 mM sodium phosphate), and 0.5 mg/ml yeast tRNA at 50° C. for 1 hour. The prehybridization buffer was removed and hybridisation solution was added, containing (in addition to the above) 10% dextran sulphate, 50 mM dithiothreitol, and $1\times10^5$ cpm/$\mu$l $^{35}$S-labelled sense or anti-sense probe. Hybridisation was carried out at 50° C. for 16–18 hours. The slides were washed twice in (2×-strength) saline sodium citrate (SSC)/14 mM β-mercaptoethanol at 50° C. for 20 minutes, rinsed in (2×-strength) SSC and treated with RNAse A (10 $\mu$g/ml) for 30 minutes at 37° C. in 0.5M NaCl, 10 mM Tris, pH 7.0, 1 mM EDTA. The slides were washed twice in double-strength SSC at room temperature for 15 minutes followed by (0.1×-strength) SSC for 60 minutes at 65° C., then dehydrated in an ethanol series. Autoradiography was carried out at 4° C. for 2–3 weeks after coating the slides in Ilford K5 emulsion. The slides were developed with Kodak K19, fixed, and counterstained with haemalum.

Immunohistochemical Staining

Cryostat sections (7–30 $\mu$m thick) were taken of ectopic and eutopic endometrial tissue, fixed in cold acetone for 10 minutes and stored at −70° C. until required. Sections for staining were thawed and air-dried before further fixing in acetone for 2 minutes. The sections were then washed in PBS and incubated for 20 minutes in 10% goat serum to block non-specific staining. Endogenous peroxidase activity was inactivated by a 10 minute incubation with 1% $H_2O_2$ in PBS. Sections were then incubated for 1 hour with either VEGF polyclonal rabbit antibody (Santa Cruz Biotechnology, Hatfield, UK) (1:300) or VEGF antibody which had been preabsorbed for 24 hours with a 10-fold excess of VEGF peptide (Santa Cruz Biotechnology, Hatfield, UK). This latter treatment served as negative control. Binding was visualised following incubation with a goat anti-rabbit biotinylated antibody (1:200) for 1 hour, and subsequent complexing with ABC (Vector, Peterborough, UK). The complex was detected with diaminobenzidine and hydrogen peroxide in 0.1M Tris-HCl (pH 7.5). Positive controls included the detection of immunostaining in chorionic plate. Macrophages in both tissue sections and isolated monocyctes and peritoneal macrophages were identified following a similar immunohistochemical staining procedure using the monoclonal antibody Leu M3 (CD14) (Houck et al., 1991 Mol. Endocrinol. 5, 1806–1814).

Acid Phosphatase

Acid phosphatase is a hydrolytic enzyme marker for macrophages and increases in its activity are associated with macrophage activation (Halme et al., 1983 Am. J. Obstet. Gynecol. 145, 333–337). Its activity was determined in peritoneal fluid, devoid of cells, from six matched endometriotic and normal patients whose tissue was used for in situ hybridisation and immunohistochemical staining. The enzyme activity was determined using a quantitative colouriinetric determination kit which measured formation of p-nitrophenol (Sigma, Poole, Dorset). Differences between the acid phosphatase activities in peritoneal fluid from endometriotic and non-endometriotic patients were analysed with the unpaired Student's t-test. P-values of 0.05 or less were considered significant.

Results

In situ hybridisation to endometriotic tissue revealed that mRNA encoding for VEGF was localised in a few individual cells within the stroma and in some of the glandular epithelium. The results are shown in FIG. 1, which shows in situ localisation of VEGF mRNA in endometriotic tissue cells and glandular epithelium. Hybridisation signal is shown by dark grains in bright field micrographs. The sections were counterstained with haemalum. Experimental sections probed with anti-sense VEGF RNA are shown in micrographs C and D. Equivalent control sections hybridised with sense control probe were negative (micrographs A and B). Messenger RNA (mRNA) encoding for the VEGF receptor, flt, was only detected, in endothelial cells lining blood vessels data not shown. The scale bar in micrographs A, C and D represents 15 $\mu$m, whereas in micrograph B it represents 38 $\mu$m. This distribution of VEGF was seen in tissue sampled during both phases ("proliferative" and "secretory") of the menstrual cycle and occurred in four out of the six endometriotic samples analysed (Table 1). The remaining two patients, one from each stage of the cycle, failed to show any significant in situ hybridisation with anti-sense probe. Paired eutopic endometrium showed some stromal and glandular epithelium hybridisation, consistent with results described previously (Charnock-Jones et al., 1993 Biol. Repro. 48, 1120–1128).

Localisation of VEGF immunoreactivity, as determined by immunohistochemical analysis, revealed a similar pattern of distribution to that observed with the in situ hybridisation in ectopic tissue. The results are shown in FIG. 2. FIG. 2 shows four micrographs (A–D): micrographs C and D show positive immunohistochemical staining for VEGF in endometriotic tissue—specifically in the stroma (C) and glandular epithelium (D). Micrographs A and B are negative controls. All sections were counterstained with haemalum. The scale bar included represents 15 $\mu$m (A and C) or 38 $\mu$m (B and D). It can be seen that individual cells within the stroma of ectopic tissue stained intensely positive, and positive staining was also evident in the glands. However few, if any, individual cells within the eutopic endometrial stroma were immunohistochemically positive for VEGF.

Immunohistochemical staining of serial endometriotic sections with the macrophage marker Leu M3 showed a strong association between the location of VEGF expressing cells and those stained positively for macrophage antigens. These results are shown in FIG. 3, which shows immunohistochemical localization of VEGF protein (micrograph C) or Leu M3 (micrograph D) in endometriotic tissue. Micrographs A and B are negative controls. The arrowed cells in C and D indicate cells which stained positive for VEGF and Leu M3 (i.e. VEGF-expressing macrophages). All sections were counter-stained with haemalum. The scale bar represents 5 $\mu$m. Few, if any, macrophages were seen in matched eutopic endometrium.

Peripheral blood monocytes are the precursors of macrophages and samples of these cells from both normal patients and those suffering from endometriosis were immunostained for VEGF protein. No peripheral blood monocytes, from either group, stained positively for VEGF protein by immunohistochemistry. Macrophages isolated from the peritoneal fluid from both groups of patients were also immunostained for VEGF protein and it was found that only patients suffering from endometriosis stained positively for VEGF. The results are shown in FIG. 4, which illustrates immunohistochemical localisation of VEGF protein in peritoneal macrophages isolated from endometriotic (micrograph C) or non-endometriotic (micrograph D) subjects. Micrographs A and B represent negative controls. All slides were counterstained with haemalum. The scale bar represents 9 μm for micrographs A and C, 5 μm for B and D.

Figure 1A:
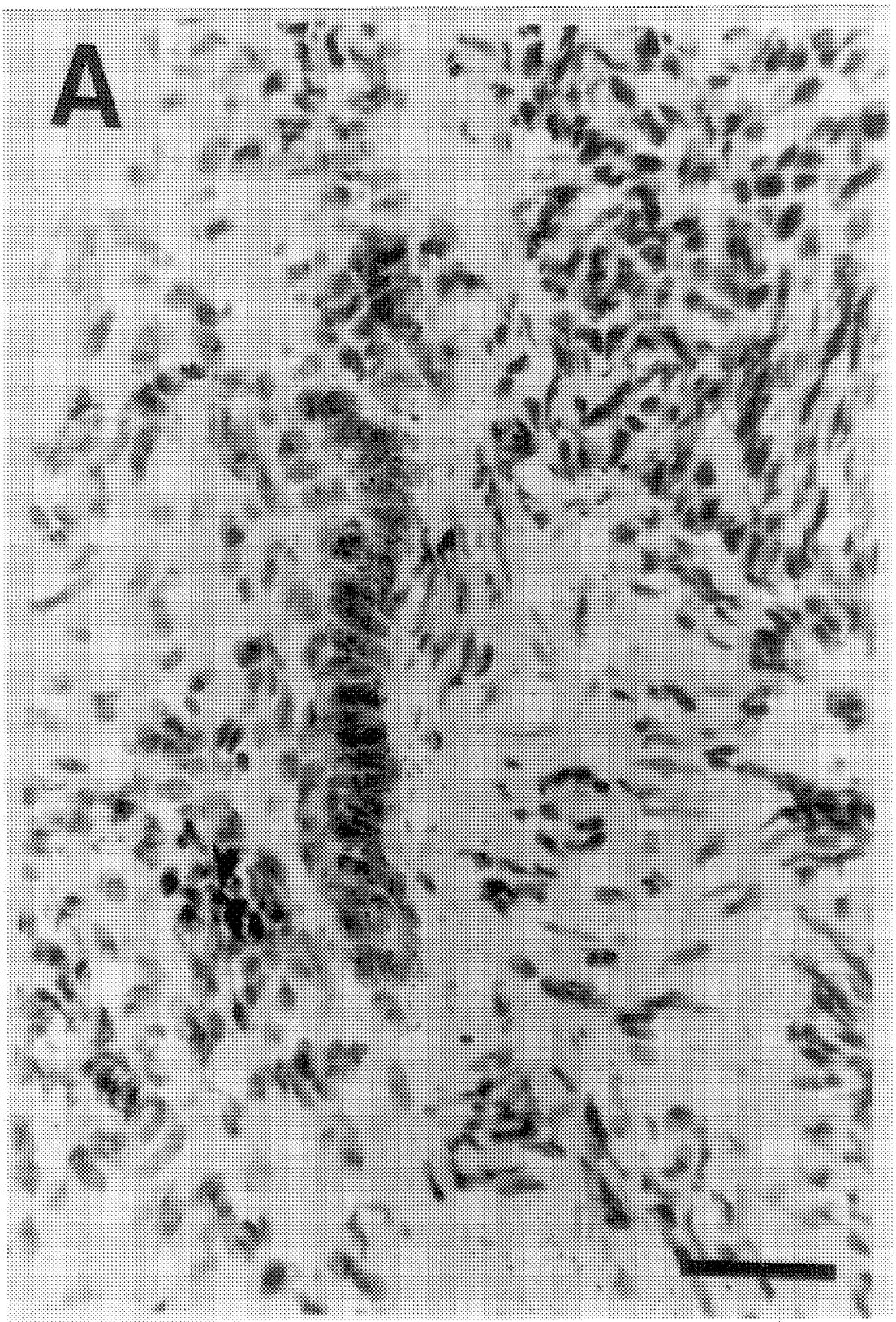
FIG. 1 shows four micrographs indicating in situ localisation of VEGF mRNA in endometriotic tissue cells and glandular epithelium.
Figure 1B:
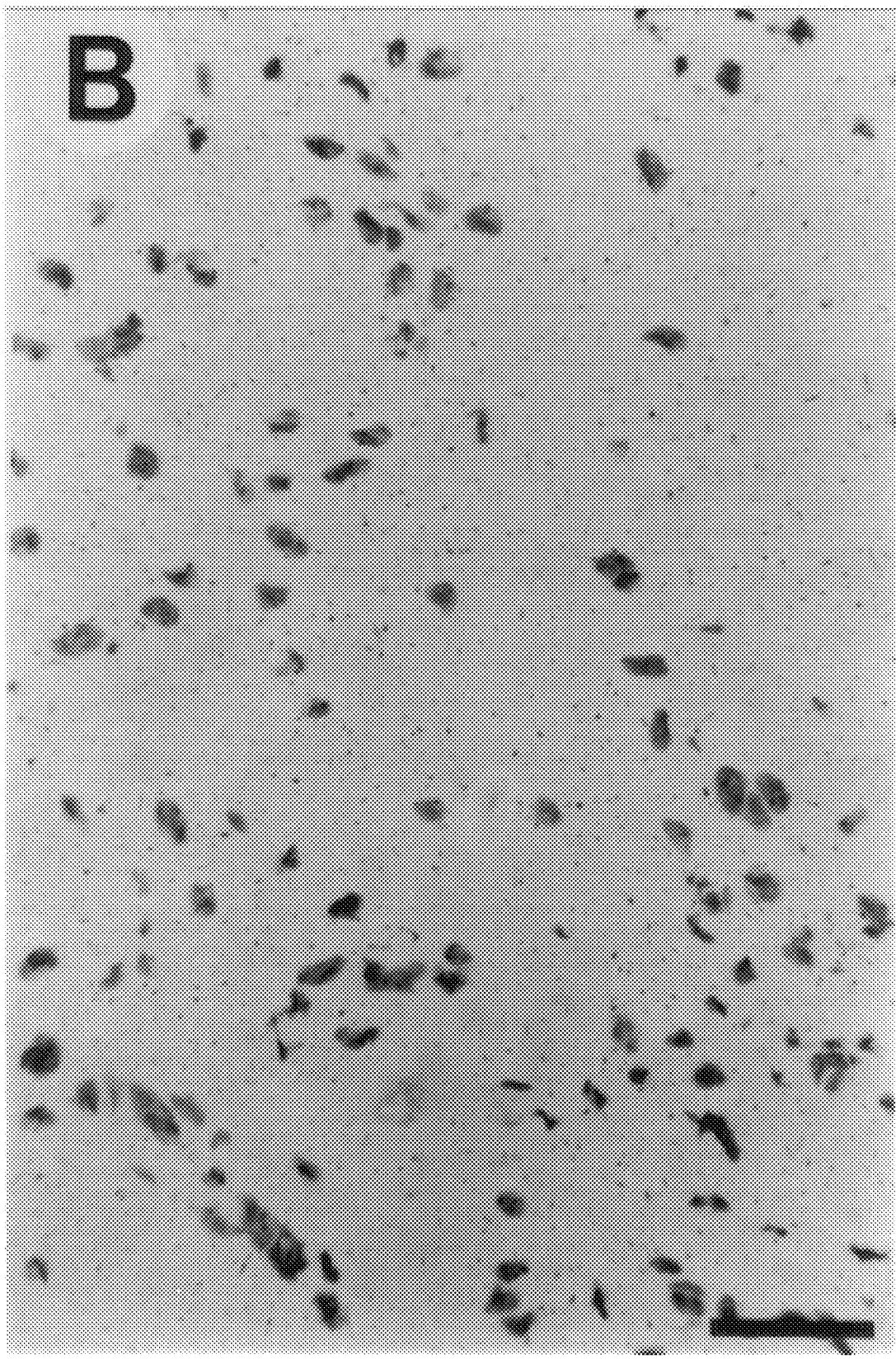
Figure 1C:
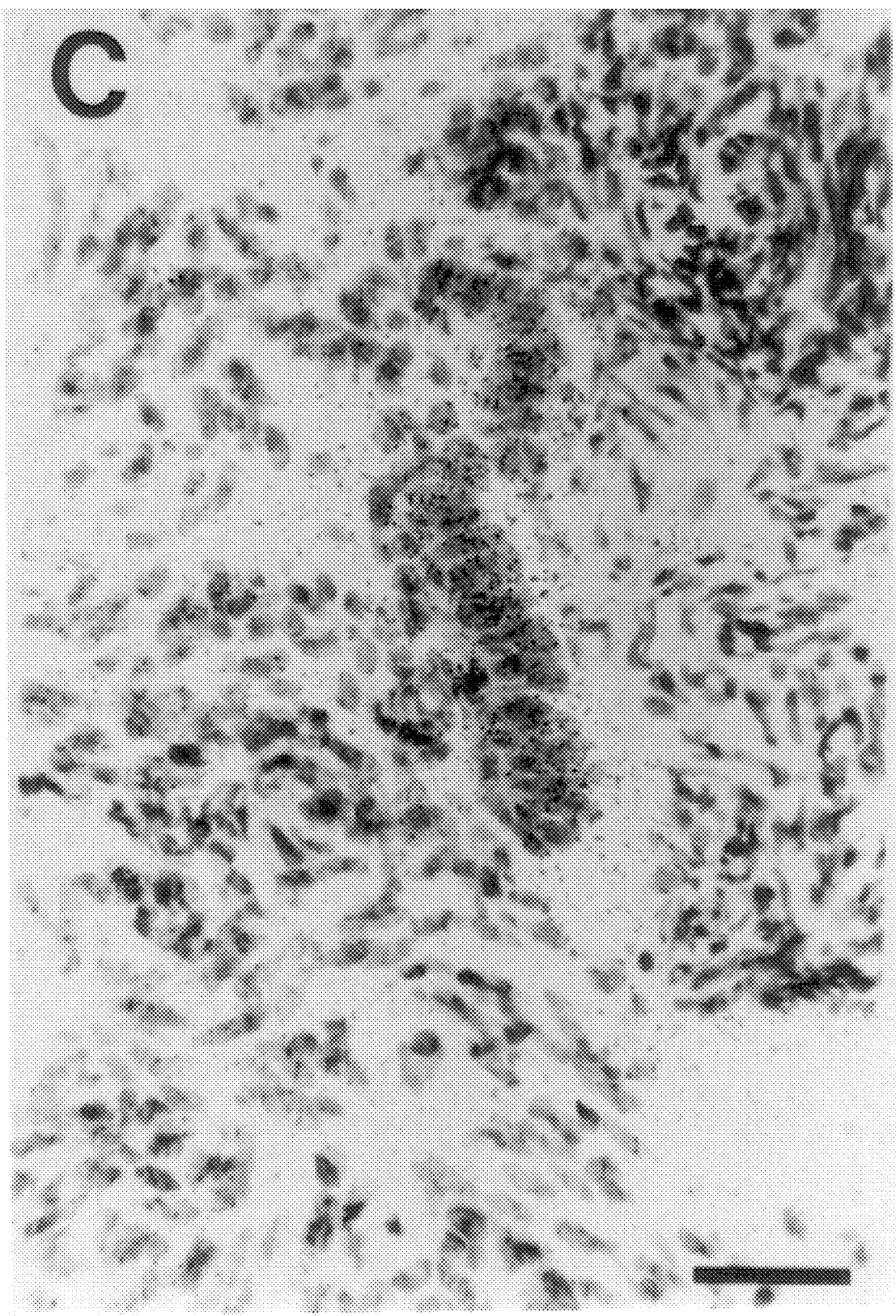
Figure 1D:
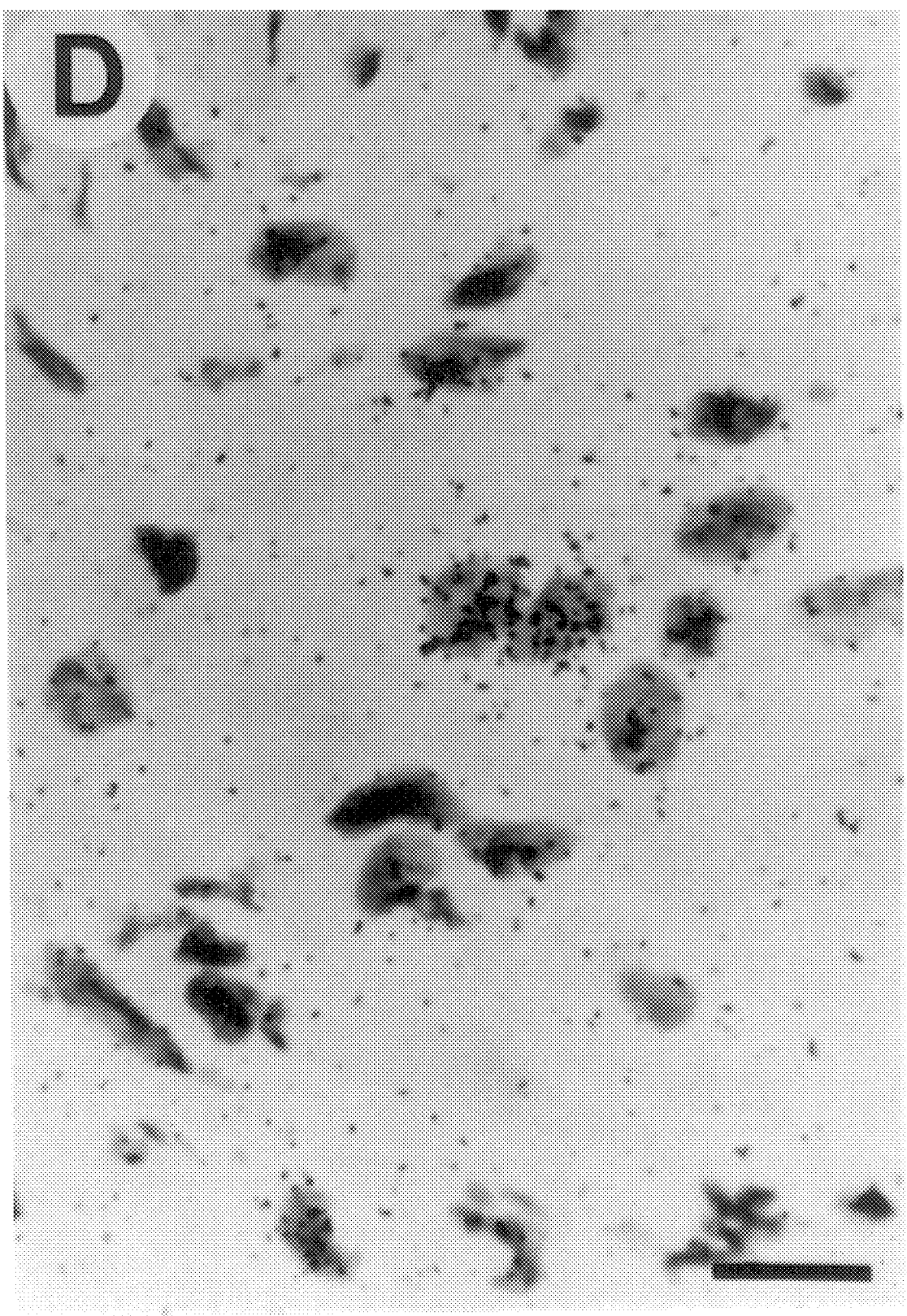
Figure 2A:
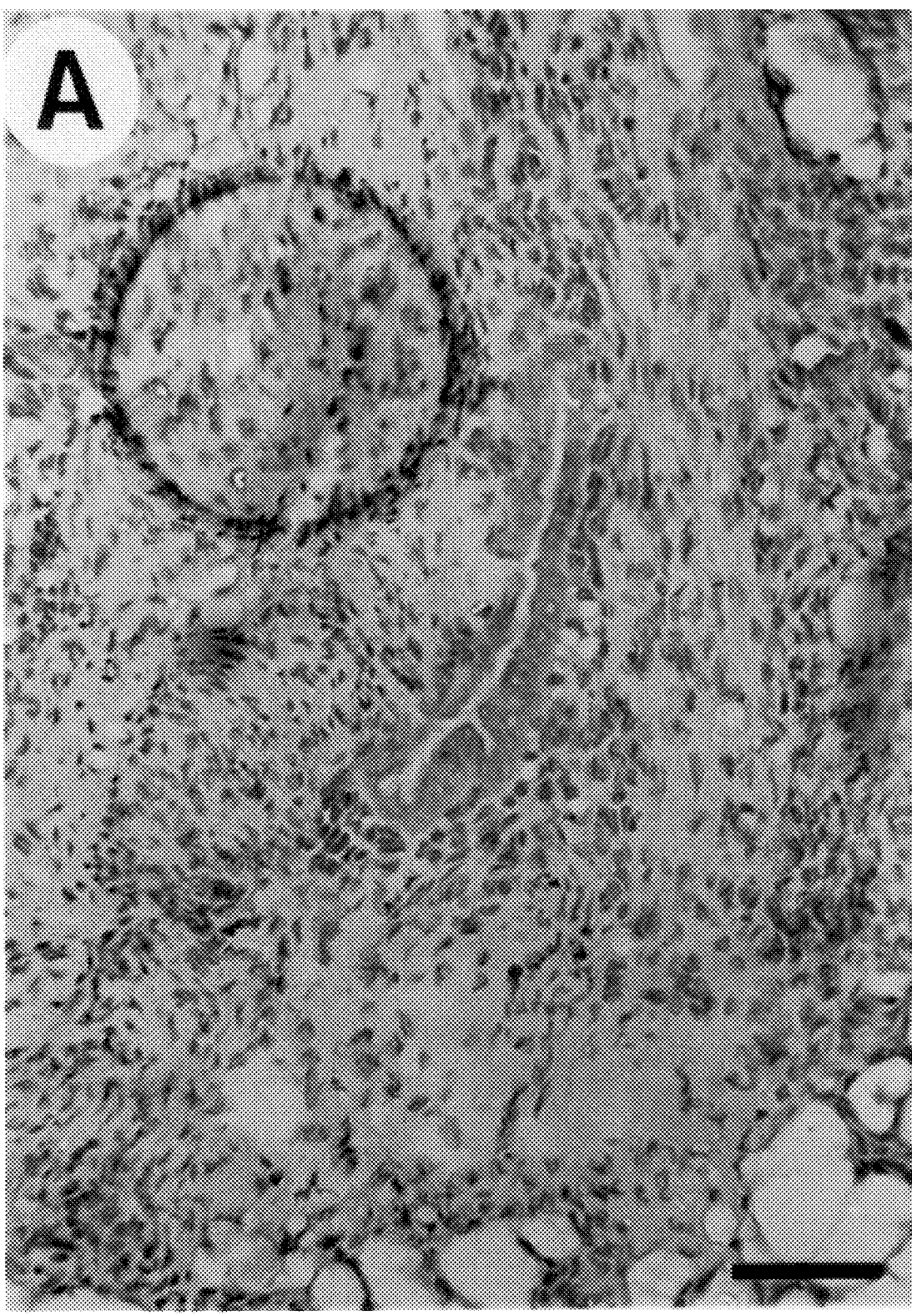
FIG. 2 shows four micrographs (A–D) of endometriotic tissue subjected to immunohistochemical staining for VEGF protein.
Figure 2B:
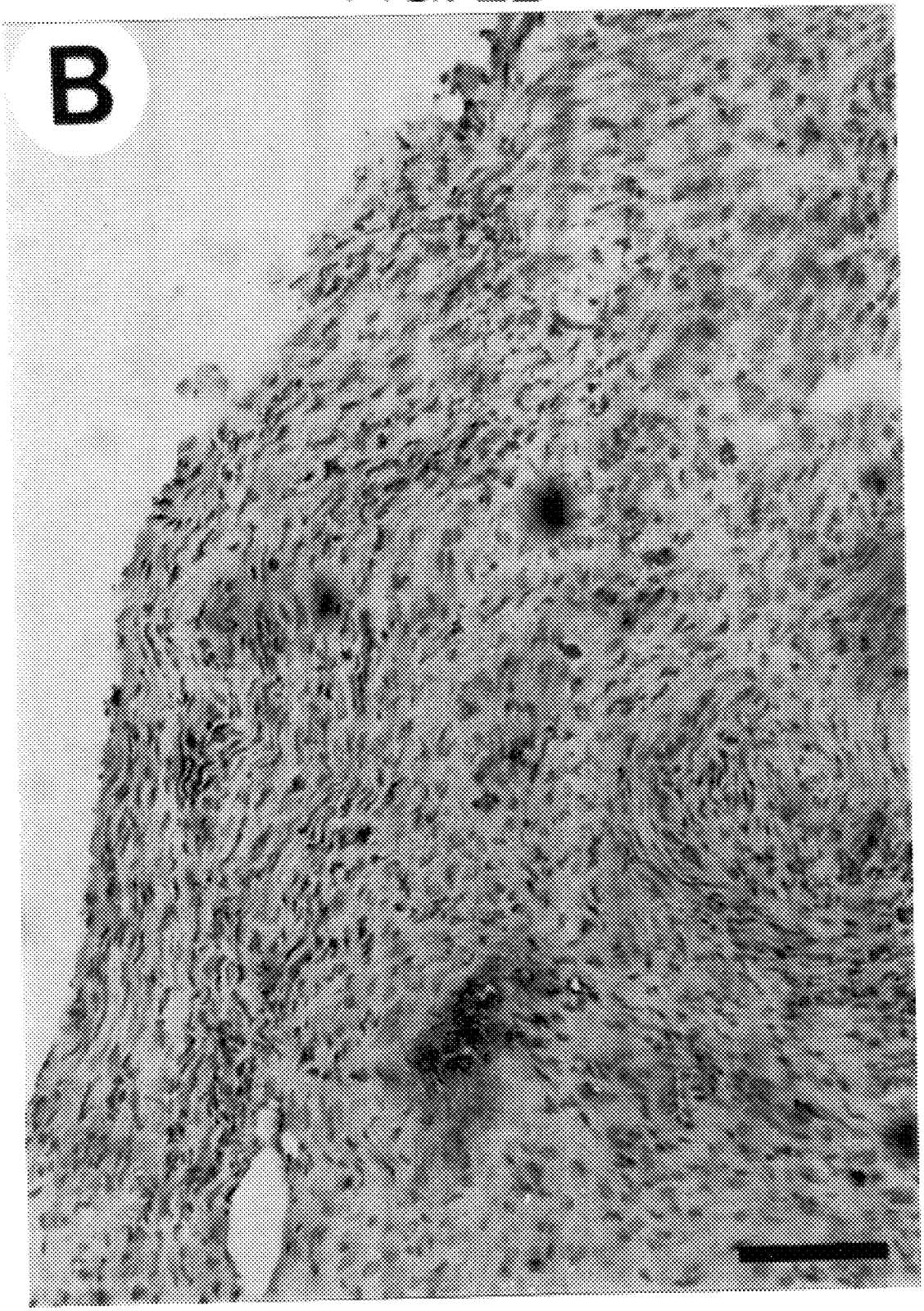
Figure 2C:
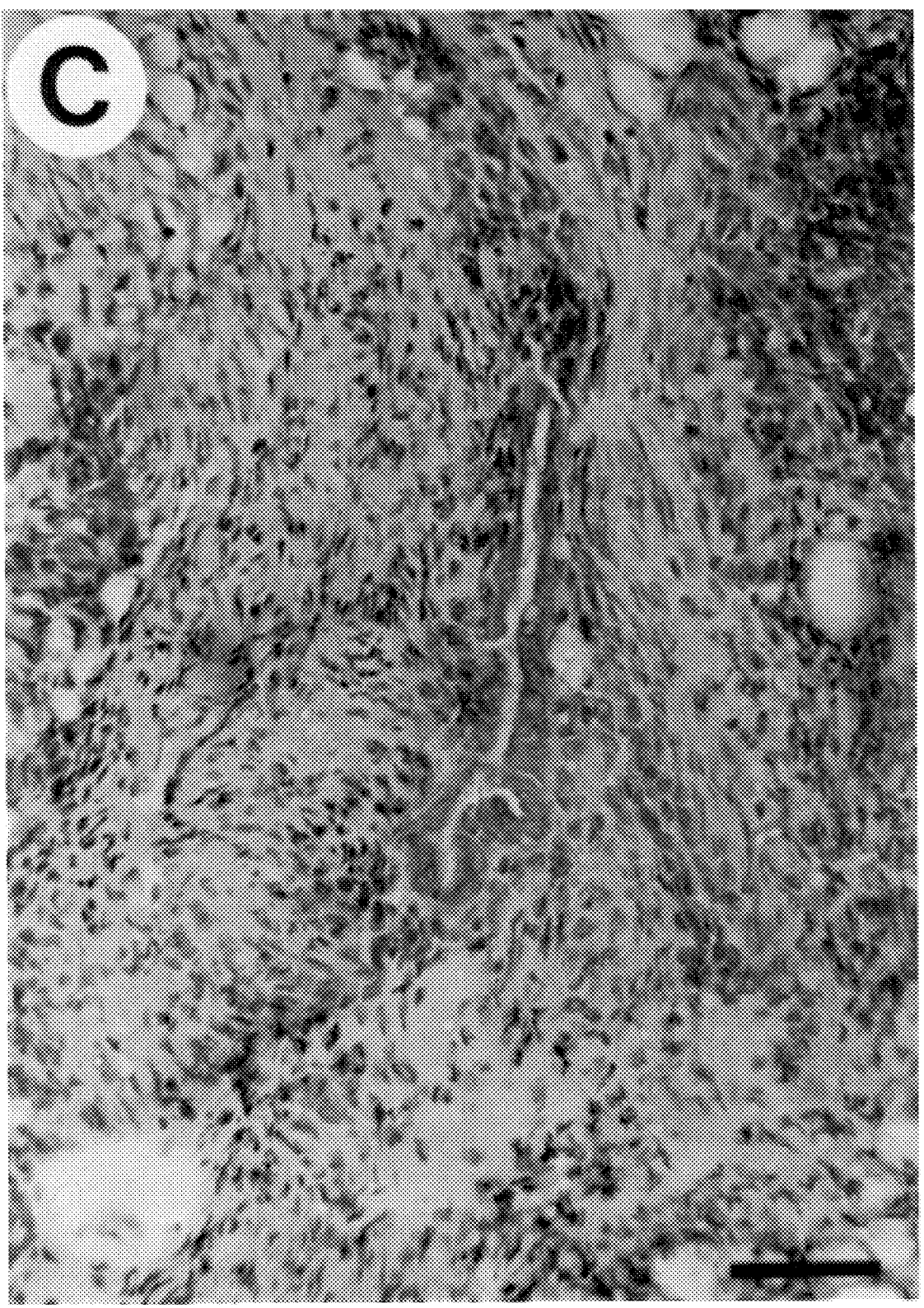
Figure 2D:
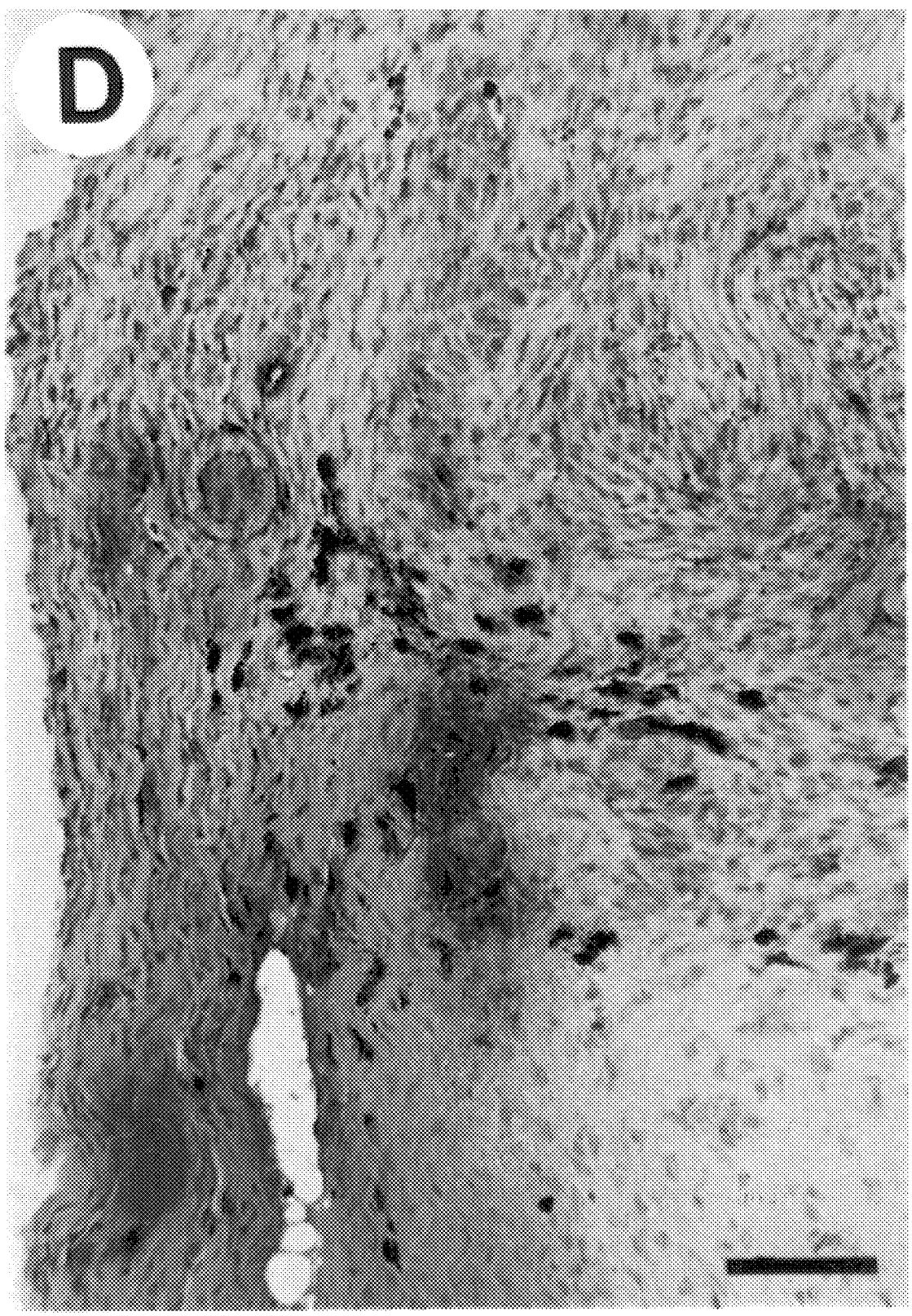
Figure 3A:
FIG. 3 shows four micrographs (A–D) of endometriotic tissue subjected to immunohistochemical staining for VEGF protein (micrograph C) or CD14 (micrograph D)
Figure 3B:
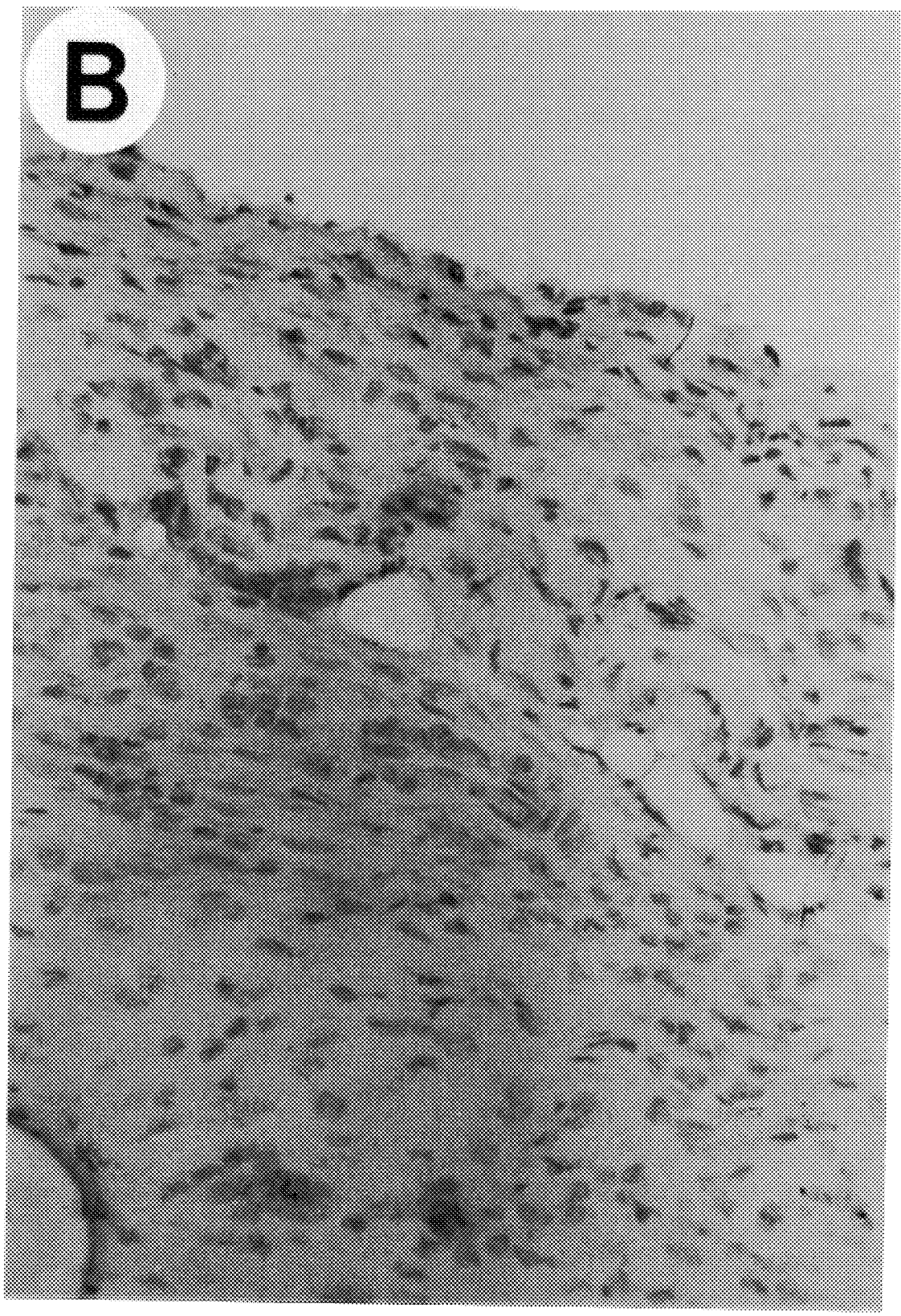
Figure 3C:
Figure 3D:
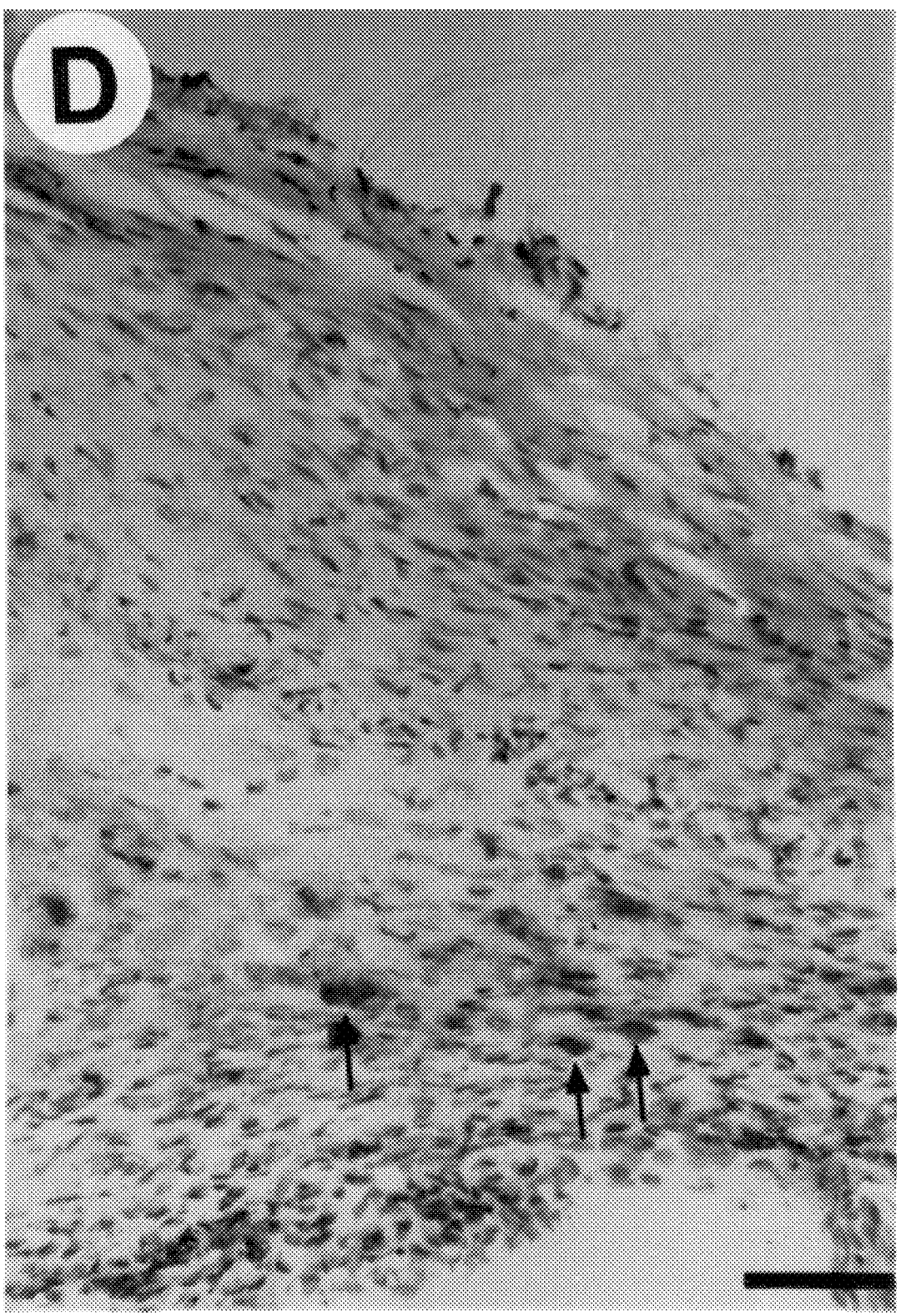
Figure 4A:
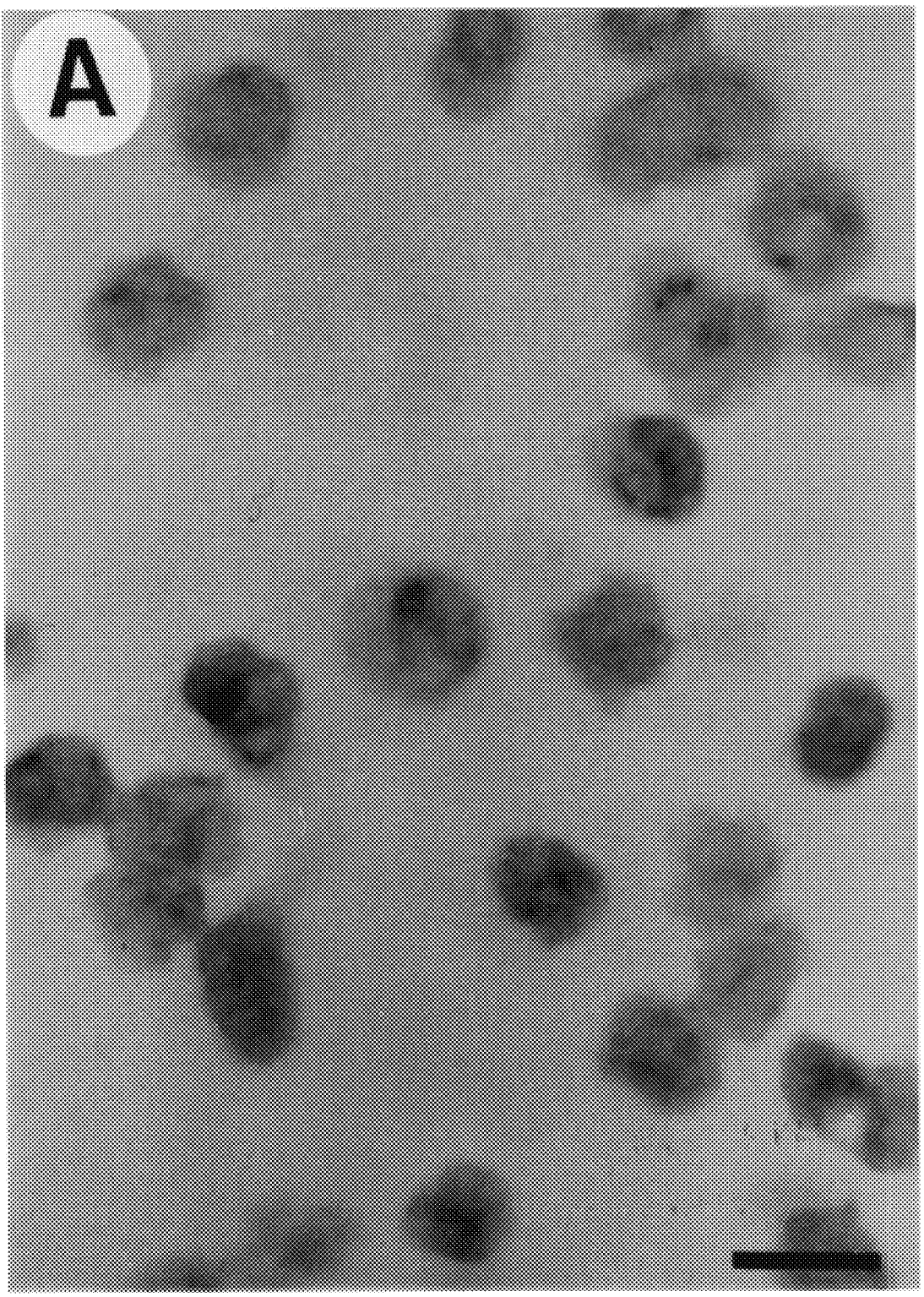
FIG. 4 shows four micrographs (A–D) of isolated peritoneal macrophages from endometriotic (micrograph C) or non-endometriotic (micrograph D) subjects, subjected to immunohistochemical staining for VEGF protein.
Figure 4B:
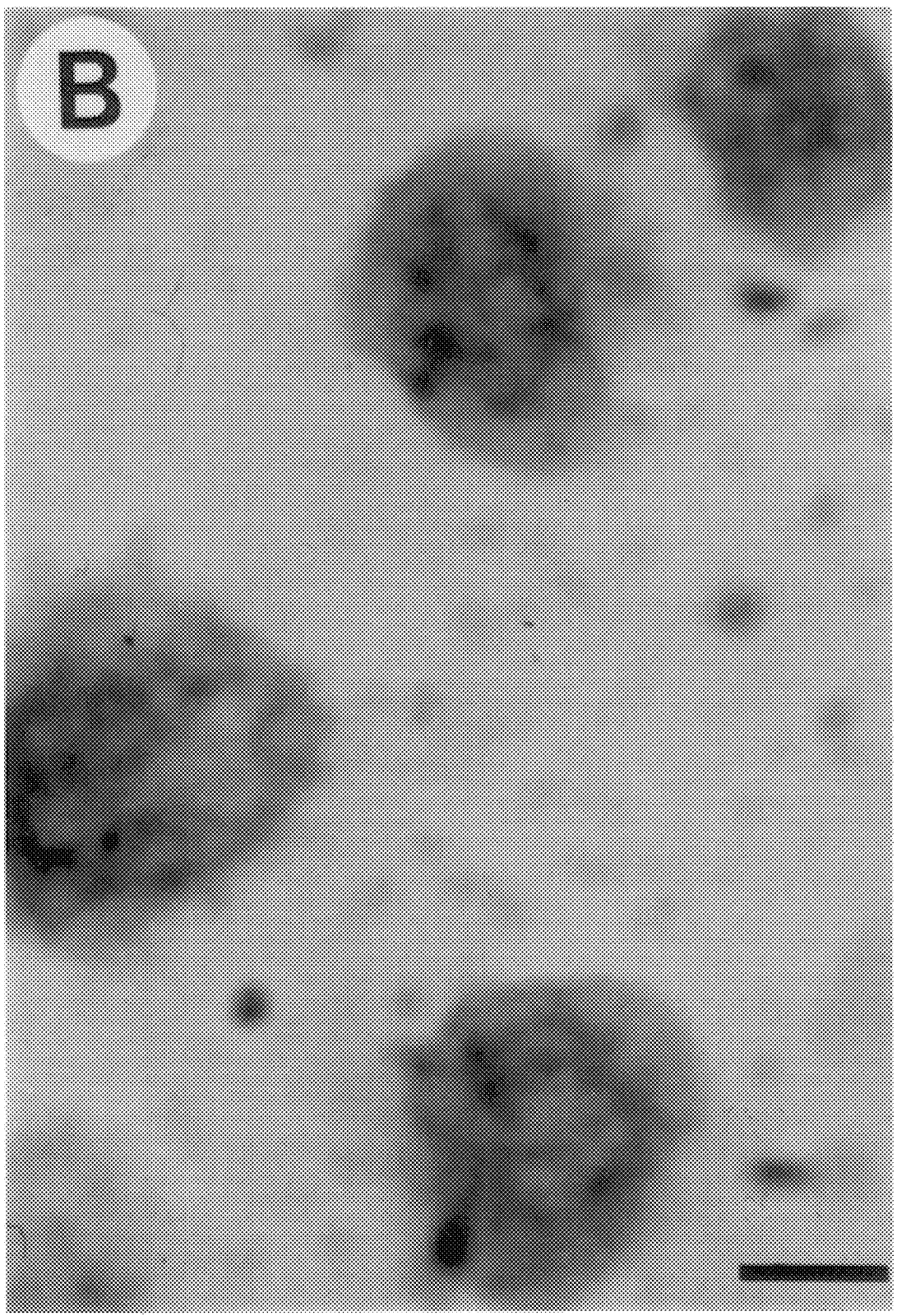
Figure 4C:
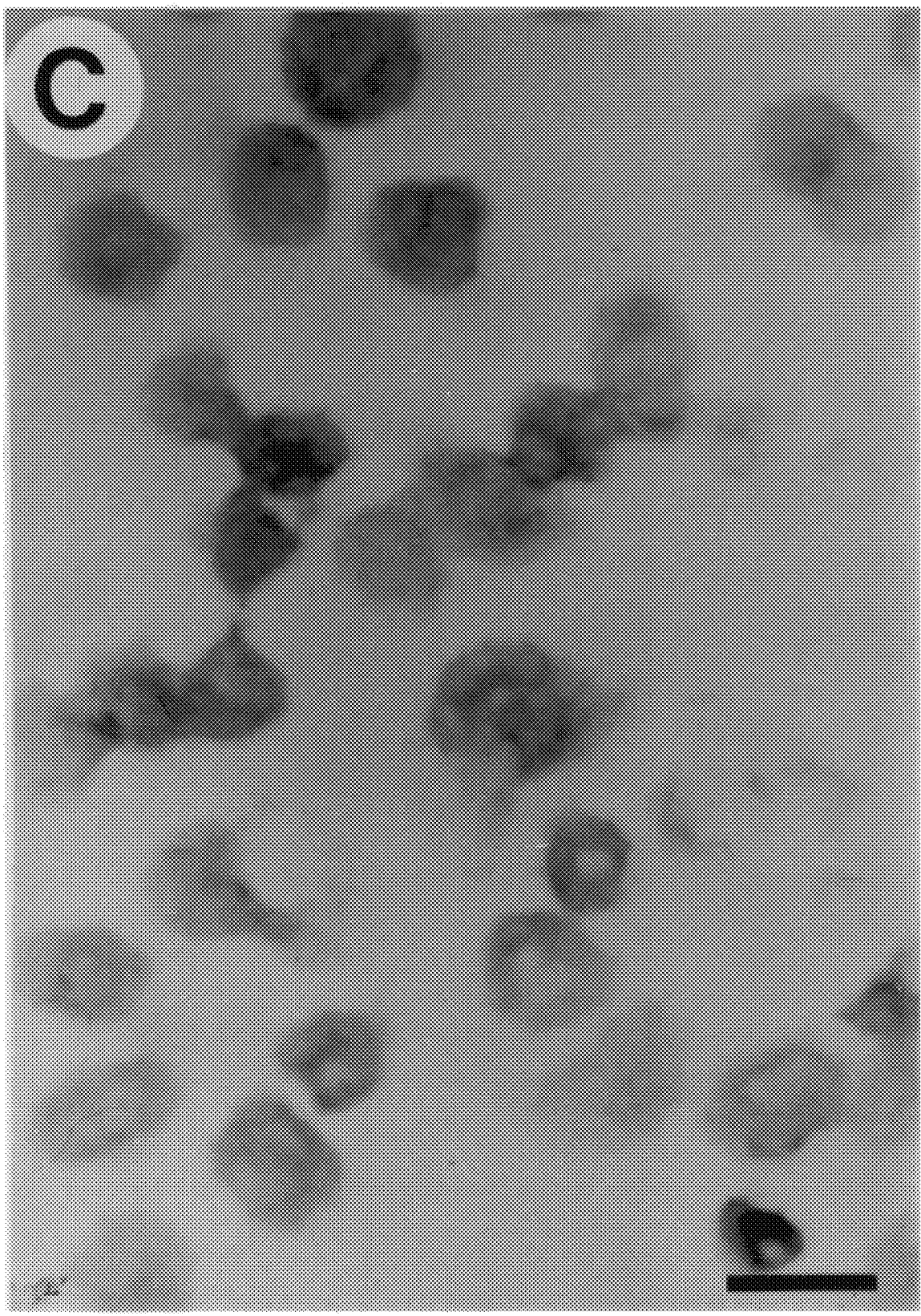
Figure 4D:
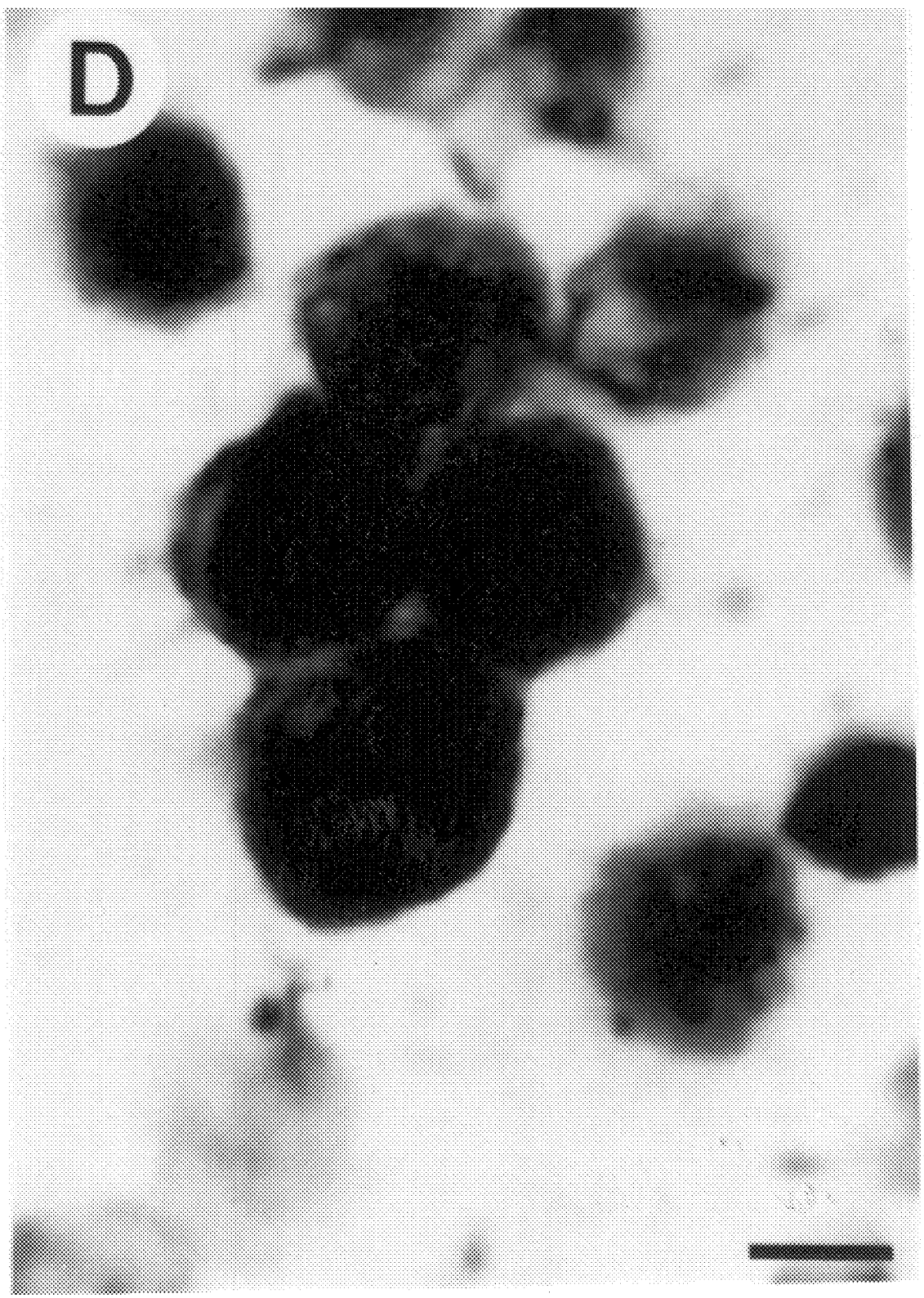
Figure 5:
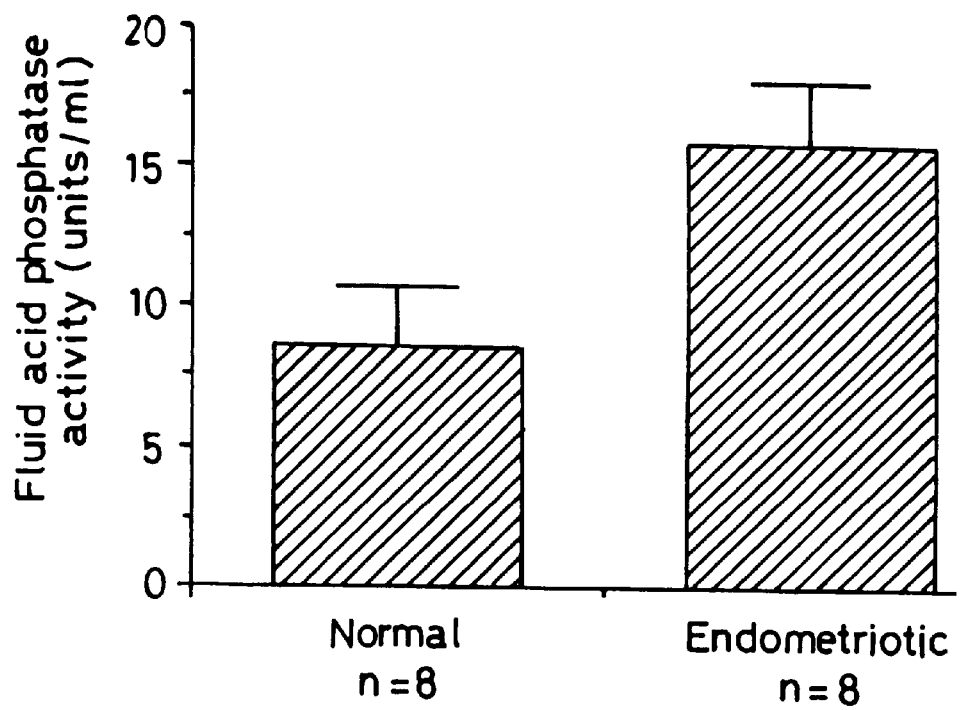
FIG. 5 is a bar chart of acid phosphatase activity (units/ml) for peritoneal fluid extracted from normal or endometriotic subjects.

Macrophage activation was assessed by acid phosphatase activity and, in summary, peritoneal fluid from endometriotic patients demonstrated a higher acid phosphatase activity (15.77±2.25 U/ml) than fluid from normal subjects (8.55±2.29 U/ml). The results are shown as a bar chart in FIG. 5. The data are expressed as units/ml of acid phosphatase activity in peritoneal fluid, ±1 standard deviation. Statistical analysis showed a significant difference ($P<0.001$) in acid phosphatase activity between peritoneal fluid from endometriotic and non-endometriotic subjects.

flt-specific and KDR-specific polymerase chain reaction (PCR) of Peritoneal Macrophage cDNA The protocol used was as described previously (Boocock et al., 1995 J. Natl. Cancer Inst. 87, 506–516).

In summary, flt receptor was detected by PCR in cDNA from all peritoneal macrophage (PM) samples tested. This included both patients with and without endometriosis. No qualitative cycle-dependent differences were detected in either patient group. Agarose gel electrophoresis of the PCR products is shown in the lower panel of FIG. 6.

KDR receptor was detected by PCR in cDNA from both patient groups. A cycle-dependent expression of the KDR receptor was evident within both groups. Both groups showed positive results with macrophages isolated from PF taken during the secretory phase of the cycle, but not from those cells isolated from proliferative phase peritoneal fluid. Agarose gel electrophoresis of the PCR products is shown in the upper panel of FIG. 6.

Figure 6:
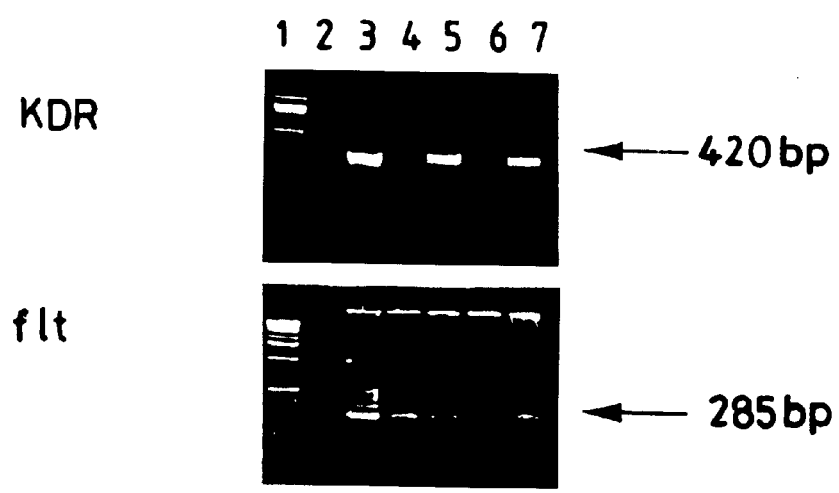
FIG. 6 is a photograph of agarose gel analysis of PCR products using primers specific for KDR (top panel) or flt (bottom panel) on cDNA prepared from peritoneal macrophages from endometriotic and normal subjects.

In both the upper and lower panels of FIG. 6, lane 1 contains molecular weight markers, lane 2 is the negative control (no cDNA added), lane 3 is the positive control (placental cDNA), lane 4 is cDNA from PM isolated from endometriotic subjects in secretory phase, lane 6 is cDNA from PM isolated from normal subjects in proliferative phase, whilst lane 7 is cDNA from PM isolated from normal subjects in secretory phase. Calculated sizes of the PCR products are indicated on the right.

flt-specific fluorescence activated cell sorting (FACS)

Protocol: Isolated PM from both patient groups were used. The cells were originally incubated in serum to block non-specific staining. These cells were then incubated for 30 minutes at 4° C. in either flt antibody (1:50) or flt antibody which had been previously preabsorbed with its original antigenic peptide. This last sample served as the control. The cells were then incubated in a FITC labelled secondary antibody (1:200) for 30 minutes at 4° C. After incubation the cells were fixed in 2% paraformaldehyde before analysis on the FACS scan. The cells were washed 2× with PBS between each stage. Determination of macrophages was achieved using the antibody Leu M3 (which is raised against CD14); this stage was done just after the removal of the secondary antibody.

The results are shown in graphs a–c of FIG. 7. FIG. 7a shows staining of the control sample, comprising cells labelled with peptide pre-absorbed anti-flt antibody, 7b staining of the experimental sample using anti-flt antibody and 7c shows cells double-staining with both anti-flt and anti-CD14. For graphs a and b, the x axis is the log fluorescence intensity of staining for flt and the y axis shows cell numbers. For graph c, the x axis is the log fluorescence intensity of staining for flt, the y axis is the log fluorescence intensity of staining for macrophages. No significant differences in the % flt positive peritoneal macrophages were seen between the two patient groups. In both groups approximately 63% of the sampled peritoneal macrophages were flt positive.

| % flt positive peritoneal macrophages | |
| --- | --- |
| Normal patient group | Endometriotic patients |
| 63 ± 11 | 63.41 ± 10.4 |
| n = 6 | n = 6 |

KDR-specific fluorescence activated cell sorting

Protocol: As described previously for flt, except the KDR antibody and its antigenic peptide were used, as appropriate.

Figure 8A:
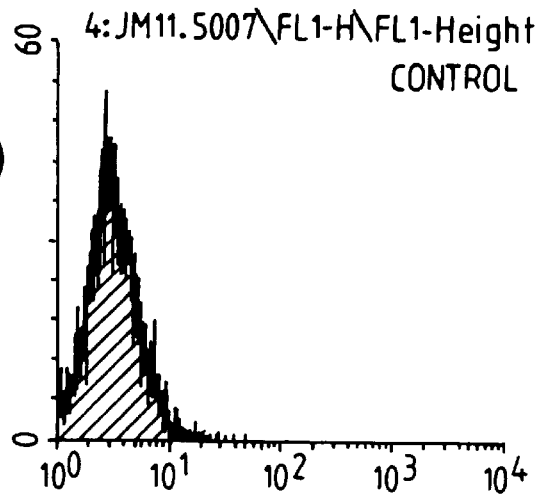
Figure 8B:
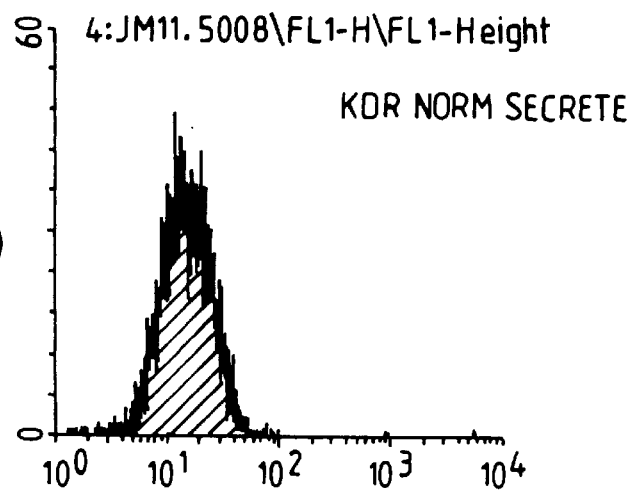
Figure 8C:
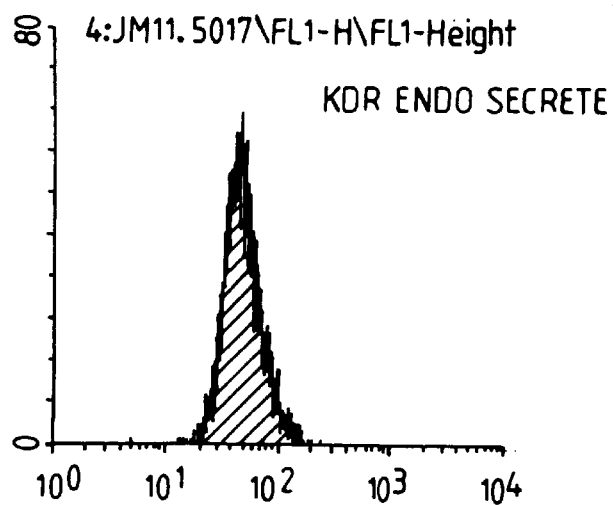

The results are shown in graphs a–c of FIG. 8.

Graph a shows the control (cells labelled with peptide pre-absorbed anti-KDR antibody), graph b shows the results for cells isolated from the secretory phase of normal subjects incubated with anti-KDR antibody, whilst graph c shows the results for cells isolated from endometriotic subjects in the secretory phase. For all graphs a–c, the x axis represents log fluorescence intensity of staining for KDR, and the y axis represents cell numbers.

A cycle-dependent variation in the number of KDR positive peritoneal macrophages was seen in both patient groups, with secretory phase PM showing the highest % of KDR positive cells. Secretory phase PM from women with endometriosis had a significantly higher % of KDR positive PM than cycle matched normals.

| % KDR positive peritoneal macrophages | | | |
| --- | --- | --- | --- |
| Normal patient group | | Endometriotic patients | |
| proliferative | secretory | proliferative | secretory |
| 4.23 ± 2.3 | 34 ± 21+ | 22.6 ± 11.7 | 78 ± 15.8++* |
| (n = 4) | (n = 6) | (n = 4) | (n = 6) |

+p < 0.01 Significantly different from normal proliferative
++p < 0.01 Significantly different from endometriotic proliferative
*p < 0.01 Significantly different from normal secretory These results are shown graphically in FIG. 9, which shows the percentage KDR+ macrophages for normal and endometriotic subjects in both the proliferative and the secretory phase of the menstrual cycle.

Chemotaxis Assay

Protocol: Isolated samples of PM from both patient groups were used. PM were exposed to various concentrations of VEGF, the cells being separated from the VEGF by a membrane. Cells containing the appropriate receptors would tend to migrate towards the VEGF and pass through the membrane. Cells which had passed through the membrane were stained and counted. Various positive and negative controls were included. Incubation time was 90 minutes at 37° C.

The results are shown in FIG. 10, which shows the chemotactic index (as a percentage of control samples) for endometriotic subjects (solid columns) or normal subjects (hatched columns) at 5, 1, 0.5 and 0.1 ng/ml (respectivelyu) of VEGF.

Only endometriotic PM (from the secretory phase of the cycle) demonstrated a significant chemotactic response to VEGF, at either 5 or 1 ng/ml VEGF (p<0.01).

VEGF concentration in peritoneal fluid from women with and without endometriosis Protocol: VEGF concentration in peritoneal fluid was determined using an ELISA system developed by the inventors. Plates were coated with a polyclonal anti-VEGF antibody (100 µg/ml) raised against complete human rVEGF$_{165}$ (Boocock et al., 1995) and incubated overnight at 4° C. and then blocked with 3% BSA in TBS for 2 hours at room temperature. Human rVEGF$_{165}$ (between 1–64 ng/ml) or PF samples were added to the coated well and incubated for 2 hours at room temperature. Plates were then incubated with biotinylated polyclonal anti-VEGF antibody. Substrate solution was added to plates. Colour was developed and the reaction stopped by the addition of sulphuric acid and absorbance at 409 nm was determined on a plate reader. The plate was washed between each step with TBS containing 0.01% Tween 20. The ELISA system was validated and optimised using VEGF spiked standards and irrelevant growth factors. Using this system the limit of sensitivity was 4 ng/ml and a standard curve was generated by plotting absorbance vs log of human VEGF concentration which was linear over a concentration range of 4–58 ng/ml.

The results are shown in FIG. 11, which shows the concentration of VEGF (ng/ml) in individual samples of peritoneal fluid from normal and endometriotic subjects in both the proliferative and the secretory phase of the menstrual cycle. VEGF was found in women with and without endometriosis. Endometriotic PF from the proliferative phase of the cycle contained significantly more VEGF than PF from the secretory phase, and from both phases of the cycle in women without endometriosis.

| Normal patient group | | Endometriotic patients | |
| --- | --- | --- | --- |
| proliferative | secretory | proliferative | secretory |
| 15 ± 8 | 15.1 ± 9.2 | 30 ± 13$^{1,2,3}$ | 10.8 ± 4.8 |

$^1$p < 0.01 significantly greater than endometriotic secretory
$^2$p < 0.01 significantly greater than normal proliferative
$^3$p < 0.01 significantly greater than normal secretory $^3$H Thymidine incorporation in HUVECs by macrophage conditioned media Protocol: Human umbilical vein endothelial cells (HUVECs) were exposed to PM conditioned media, and the uptake of $^3$H thymidine determined. This provides an indication of endothelial cell proliferation. Inhibition studies using a specific anti-VEGF antibody allowed the contribution of VEGF to PM induced endothelial cell proliferation to be assessed.

The results are shown in the bar chart in FIG. 12. The chart shows tritiated thymidine incorporation (as a percentage of control samples) for HUVECs exposed to medium conditioned by PM from endometriotic subjects (left hand columns) or normal subjects (right hand columns). The solid columns are PM-conditioned medium only, whilst the hatched columns show the results obtained with PM-conditioned medium treated with anti-VEGF antibody. The single + sign denotes significantly greater $^3$H incorporation (P<0.05) compared to controls; ++ denotes significantly less $^3$H incorporation (P<0.05) compared to endometriotic macrophage conditioned medium; and ** denotes significantly greater $^3$H incorporation (P<0.05) compared to normal macrophage conditioned medium.

Conditioned media from both groups produced a stimulation of $^3$H thymidine which was significantly greater than the control. Endometriotic media produced a stimulation of $^3$H thymidine incorporation significantly greater than that shown by normal media, and was the only group to have this incorporation significantly reduced by the action of anti-VEGF.

From the foregoing, one can conclude:
a) that VEGF is present in peritoneal fluid (as shown by HUVEC culture and ELISA results);
b) that there is more VEGF in peritoneal fluid of patients with endometriosis than in normal subjects;
c) that VEGF is produced by i) endomitotic tissue implants and ii) (predominantly) by peritoneal macrophages
d) VEGF receptors flt and KDR are present on peritoneal macrophages and that
i) flt mRNA (as judged by RT-PCR) is present throughout the menstrual cycle,
ii) KDR mRNA (as judged by RT-PCR) is present only in the secretory phase
e) from the results of FACS analysis:
i) flt immunoreactivity does not change during the menstrual cycle
ii) the KDR+ population increases significantly in the secretory phase
iii) KDR is elevated in patients with endometriosis
f) the chemotactic response to VEGF of peritoneal macrophages is significantly elevated only in the secretory phase, and only in cells isolated from patients with endometriosis.

The present inventors accordingly suggest that VEGF may be involved in the pathology of endometriosis not only via its effects on angiogenesis but also via its effects on macrophage function (e.g. activation status, migration, protease and/or cytokine release).

Discussion

The pathogenesis of endometriosis is unknown. Endometrium can be widely disseminated by a number of mechanisms, however both clinical and experimental evidence point towards retrograde menstruation as being the most likely mechanism by which endometrium enters the peritoneal cavity (Lieu & Hitchcock 1968, cited previously; and Blumenkrantz et al., 1981 Obstet. Gynecol. 57, 667). Apart from ovarian hormones little is known of the other factors which may lead to endometrial implantation.

Peritoneal macrophages which differentiate from peripheral monocytes are known to be increased in number and activation in women with endometriosis (Halme et al., 1983; Olive et al., both cited previously). In this study peritoneal macrophages from endometriotic patients stained intensely for VEGF and in situ hybridisation demonstrated significant amount of mRNA, but peritoneal macrophages from normal patients and circulating monocytes from both patient groups did not stain positive for VEGF.

The finding of lower acid phosphatase activity in normal patients indicates a lower activation status than in endometriotics, suggesting that activation is a requirement for the synthesis of VEGF. Therefore, the activation status of peritoneal macrophages may be a decisive factor in the pathogenesis of endometriosis, especially in terms of VEGF expression and angiogenesis. Recently, however, it has been suggested that monocytes, from endometriotic patients, may have a direct stimulatory effect on endometrial cell proliferation in culture (Braun et al., 1994 Fertil. Steril. 61, 78–84), thereby suggesting that for endometrial cell proliferation at least, monocyte maturation-activation may not be the only mechanism.

This present study demonstrated the localisation of mRNA encoding for VEGF in individual cells within the stroma and glandular epithelium of endometriotic tissue. The similar localisation of the VEGF peptide, by immunohistochemical staining, confirms the presence of this peptide within this tissue. Staining of serial sections with the antibody Leu M3 and by morphology indicate these VEGF producing cells are almost certainly macrophages. These cells could have been resident within the eutopic endometrium before it was deposited into the peritoneal cavity.

Alternatively, peritoneal fluid macrophages could infiltrate the ectopic tissue. In this study immunohistochemical staining failed to identify any population of macrophages expressing VEGF in matched eutopic endometrium, suggesting that the VEGF expressing macrophages found in the ectopic endometriotic tissue originated from another source. More likely these macrophages may have infiltrated from the peritoneal fluid. Klein and workers (1993, Am. J. Human Repro. 30, 74–81) recently showed an increase in resident leukocytes in endometriotic tissue compared to normal tissue, and concluded that they originated from the peritoneal population of leukocytes. Secondly, endometriotic tissue can secrete factors such as interferon-γ (Klein et al., cited above) which is chemotactic for leukocytes (Tabibzadeh 1991, cited previously). In addition, VEGF itself is chemotactic for leukocytes (Clauss et al., 1990 J. Exp. Med. 172, 1535–1545) which in this study was shown to be secreted in endometriotic glandular epithelium. Thirdly, we have shown that peritoneal fluid from women with endometriosis contained a population of VEGF expressing macrophages. Given these observations, infiltrations of VEGF secreting macrophages into the ectopic endometrium is a distinct possibility.

In conclusion, VEGF has been shown to be expressed in endometriotic tissue, with immunostaining seen most intensely in macrophage positive cells, and to a lesser extent in glandular epithelium. Our studies with isolated macrophages and monocytes suggest that only peritoneal macrophages from women with endometriosis, produce VEGF. This may lead to elevated levels of this potent angiogenic factor in peritoneal fluid of endometriotics, and to infiltration of ectopic endometriotic tissue by VEGF producing macrophages. Both events may be crucial to the successful implantation and maintenance of endometriotic explants through the increase in VEGF resulting in vascularisation both within the ectopic tissue and the surrounding peritoneum.

What is claimed is:

1. A method of treating endometriosis comprising administering to a woman an effective amount of a polypeptide capable of interfering with the production or activity of VEGF;

wherein the polypeptide is a soluble truncated form of the flt or KDR receptor which binds to VEGF and acts as an antagonist thereto; and wherein the polypeptide is capable of inhibiting the effect of VEGF on a target selected from the group consisting of endometriotic tissue, a macrophage in the endometriotic tissue, a macrophage around endometriotic tissue, and a macrophage in peritoneal fluid.

2. The method of claim 1, wherein the polypeptide is administered by an intra-uterine or intra-peritoneal route.

3. A method of treating endometriosis comprising administering to a woman an effective amount of a polypeptide capable of interfering with the production or activity of VEGF;

wherein the polypeptide is an anti-VEGF antibody or an effective portion thereof; and wherein the polypeptide is capable of inhibiting the effect of VEGF on a target selected from the group consisting of endometriotic tissue, a macrophage in the endometriotic tissue, a macrophage around endometriotic tissue, and a macrophage in peritoneal fluid.

4. The method of claim 3, wherein the polypeptide is administered by an intra-uterine or inter-peritoneal route.

* * * * *